United States Patent
Matsumoto et al.

(10) Patent No.: US 9,456,745 B2
(45) Date of Patent: Oct. 4, 2016

(54) FUNDUS OBSERVATION APPARATUS AND FUNDUS IMAGE ANALYZING APPARATUS

(71) Applicants: Kyoto University, Kyoto-shi (JP); KABUSHIKI KAISHA TOPCON, Itabashi-ku (JP)

(72) Inventors: Akiko Matsumoto, Asaka (JP); Yugo Kimura, Kyoto (JP); Masanori Hangai, Kyoto (JP); Nagahisa Yoshimura, Kyoto (JP); Tsutomu Kikawa, Adachi-ku (JP); Akihiko Sekine, Inagi (JP)

(73) Assignees: KYOTO UNIVERSITY, Kyoto-shi (JP); KABUSHIKI KAISHA TOPCON, Itabashi-ku (JP)

( * ) Notice: Subject to any disclaimer, the term of this patent is extended or adjusted under 35 U.S.C. 154(b) by 225 days.

(21) Appl. No.: 14/382,199

(22) PCT Filed: Jan. 21, 2013

(86) PCT No.: PCT/JP2013/051098
§ 371 (c)(1),
(2) Date: Aug. 29, 2014

(87) PCT Pub. No.: WO2013/128975
PCT Pub. Date: Sep. 6, 2013

(65) Prior Publication Data
US 2015/0116660 A1    Apr. 30, 2015

(30) Foreign Application Priority Data

Feb. 29, 2012 (JP) ................................ 2012-042920

(51) Int. Cl.
*A61B 3/12* (2006.01)
*A61B 3/10* (2006.01)
(Continued)

(52) U.S. Cl.
CPC ............... *A61B 3/12* (2013.01); *A61B 3/0058* (2013.01); *A61B 3/102* (2013.01); *A61B 3/14* (2013.01);
(Continued)

(58) Field of Classification Search
CPC .......... A61B 3/14; A61B 3/102; A61B 3/12; A61B 3/1005; A61B 5/0066; A61B 5/14555
USPC ................................ 351/206, 246, 205, 200
See application file for complete search history.

(56) References Cited

U.S. PATENT DOCUMENTS

| 6,377,349 B1 | 4/2002 | Fercher |
| 2003/0114740 A1 | 6/2003 | Essock et al. |

(Continued)

FOREIGN PATENT DOCUMENTS

| JP | 9 276232 | 10/1997 |
| JP | 11 325849 | 11/1999 |

(Continued)

OTHER PUBLICATIONS

International Search Report Issued Feb. 12, 2013 in PCT/JP13/051098 Filed Jan. 21, 2013.

(Continued)

*Primary Examiner* — Hung Dang
(74) *Attorney, Agent, or Firm* — Oblon, McClelland, Maier & Neustadt, L.L.P

(57) ABSTRACT

In a fundus observation apparatus, an optical system detects interference light generated by superposing signal light having traveled by way of an eye fundus and reference light having traveled by way of a reference optical path. An image forming part forms a cross sectional image based on detection results of the interference light. A specifying part analyzes the cross sectional image to specify an abnormal region located in the vicinity of central fovea of the eye fundus. The association information generating part calculates the distance between the central fovea and the abnormal region and generates association information in which the direction of the abnormal region relative to the central fovea and the distance are associated with each other. The evaluation information generating part generates evaluation information for evaluating the state of the eye fundus based on the association information.

27 Claims, 13 Drawing Sheets

(51) Int. Cl.
*A61B 3/14* (2006.01)
*G06T 7/00* (2006.01)
*A61B 3/00* (2006.01)

(52) U.S. Cl.
CPC ............ *G06T 7/0012* (2013.01); *A61B 3/0025* (2013.01); *A61B 3/1005* (2013.01); *G06T 2207/10101* (2013.01); *G06T 2207/30041* (2013.01)

(56) References Cited

U.S. PATENT DOCUMENTS

| | | |
|---|---|---|
| 2004/0258285 A1 | 12/2004 | Hansen et al. |
| 2006/0100528 A1 | 5/2006 | Chan et al. |
| 2008/0309881 A1 | 12/2008 | Huang et al. |
| 2010/0002192 A1 | 1/2010 | Hara |
| 2010/0202677 A1 | 8/2010 | Imamura et al. |
| 2010/0290005 A1 | 11/2010 | Huang et al. |
| 2011/0279775 A1 | 11/2011 | Hong |
| 2011/0304821 A1* | 12/2011 | Tanassi ................ A61B 3/0091 351/206 |
| 2012/0070059 A1 | 3/2012 | Furukawa et al. |
| 2012/0120368 A1 | 5/2012 | Fujimora et al. |
| 2012/0121158 A1 | 5/2012 | Sekine et al. |
| 2012/0127427 A1 | 5/2012 | Guo et al. |
| 2013/0148081 A1* | 6/2013 | Tanaka ................... A61B 3/102 351/206 |

FOREIGN PATENT DOCUMENTS

| | | |
|---|---|---|
| JP | 2002 139421 | 5/2002 |
| JP | 2006 153838 | 6/2006 |
| JP | 2007 24677 | 2/2007 |
| JP | 2008 73099 | 4/2008 |
| JP | 2008 259544 | 10/2008 |
| JP | 2008 272256 | 11/2008 |
| JP | 2009 89792 | 4/2009 |
| JP | 2010 88541 | 4/2010 |
| JP | 2010 529896 | 9/2010 |
| JP | 2011 24930 | 2/2011 |
| JP | 2011 72716 | 4/2011 |
| WO | WO 00/51080 A1 | 8/2000 |
| WO | 2006 022045 | 3/2006 |
| WO | WO 2008/077412 A1 | 7/2008 |
| WO | 2010 044184 | 4/2010 |
| WO | WO 2010/140477 A1 | 12/2010 |
| WO | 2011 013314 | 2/2011 |
| WO | WO 2011/013315 A1 | 2/2011 |
| WO | WO 2012/068408 A1 | 5/2012 |

OTHER PUBLICATIONS

Partial Supplementary Search Report issued Nov. 12, 2015 in European Patent Application No. 13755334.3.
Extended European Search Report issued Mar. 10, 2016 in Patent Application No. 13755334.3.

* cited by examiner

FUNDUS OBSERVATION APPARATUS AND FUNDUS IMAGE ANALYZING APPARATUS

TECHNICAL FIELD

The present invention relates to a fundus observation apparatus that obtains an image of an eye fundus by using optical coherence tomography (OCT) and a fundus image analyzing apparatus that analyzes an image of an eye fundus.

BACKGROUND TECHNOLOGY

In recent years, OCT that forms images of the surface morphology and internal morphology of an object by using a light beam from a laser light source or the like has attracted attention. Unlike an X-ray CT apparatus, optical coherence tomography is noninvasive to human bodies, and is therefore expected to be utilized in the medical field and biological field. For example, in the ophthalmology, apparatuses that form images of a fundus and cornea or the like are in a practical stage.

The apparatus disclosed in Patent Document 1 uses a technique of so-called "Fourier Domain OCT." That is to say, the apparatus irradiates a low-coherence light beam to an object, superposes the reflected light and the reference light to generate an interference light, and acquires the spectral intensity distribution of the interference light to execute Fourier transform, thereby imaging the morphology in the depth direction (the z-direction) of the object. Furthermore, the apparatus is provided with a galvano mirror that scans a light beam (signal light) along one direction (x-direction) perpendicular to the z-direction, and is thereby configured to form an image of a desired measurement target region of the object. An image formed by this apparatus is a two-dimensional cross sectional image in the depth direction (z-direction) along the scanning direction (x-direction) of the light beam. The technique of this type is also called Spectral Domain.

Patent Document 2 discloses a technique of scanning with a signal light in the horizontal direction (x-direction) and the vertical direction (y-direction) to form multiple two-dimensional cross sectional images in the horizontal direction, and acquiring and imaging three-dimensional cross sectional information of a measured range based on the cross sectional images. As the three-dimensional imaging, for example, a method of arranging and displaying multiple cross sectional images in the vertical direction (referred to as stack data or the like), or a method of executing a rendering process on volume data (voxel data) based on stack data to form a three-dimensional image may be considered.

Patent Documents 3 and 4 disclose other types of OCT apparatuses. Patent Document 3 describes an OCT apparatus that images the morphology of an object by sweeping the wavelength of light that is irradiated to an object (wavelength sweeping), detecting interference light obtained by superposing the reflected lights of the light of the respective wavelengths on the reference light to acquire its spectral intensity distribution, and executing Fourier transform. Such an OCT apparatus is called a Swept Source type or the like. The Swept Source type is a kind of the Fourier Domain type.

Further, Patent Document 4 describes an OCT device that irradiates a light having a predetermined beam diameter to an object and analyzes the components of an interference light obtained by superposing the reflected light and the reference light, thereby forming an image of the object in a cross-section orthogonal to the travelling direction of the light. Such an OCT device is called a full-field type, en-face type or the like.

Patent Document 5 discloses an example of applying OCT to the ophthalmologic field. It should be noted that, before OCT was applied, a retinal camera, a slit lamp microscope, etc. were used as apparatuses for observing an eye (see Patent Documents 6 and 7, for example). The retinal camera is an apparatus that photographs the fundus by projecting illumination light onto the eye and receiving the reflected light from the fundus. The slit lamp microscope is an apparatus that obtains an image of the cross-section of the cornea by cutting off the light section of the cornea using slit light.

The apparatus with OCT is superior relative to the retinal camera, etc. in that high-definition images can be obtained, further in that cross sectional images and three-dimensional images can be obtained, etc.

Thus, the apparatus using OCT can be used for observation of various regions of the eye and is capable of obtaining high-definition images, and therefore, has been applied to the diagnosis of various ophthalmic disorders.

Now, there are three important viewpoints in ophthalmological practice. They are "early detection", "center management" and "progression management". Although early detection and progression management are thought to be important in other medical department, center management is specific to ophthalmology. There is a site called central fovea in an eye fundus. The central fovea is located at the center of the macula area of a retina, contributes to eyesight at the central visual field with high resolution, and is a most important region in the eye fundus. Thus, it is judged whether or not a disease exists in a near-field of the central fovea, and treatment plan is determined according to the judgment. This is center management. For example, medical diagnosis and treatment for glaucoma is carried out by especially focusing on the state of the area within 5 degrees around central fovea. A perimeter is used for the examination for this purpose (see Patent Document 8, for example).

Further, it is also carried out to acquire information of an eye fundus (in particular, thickness of a layer in an eye fundus) by using OCT (see Patent Documents 9, 10 and 11, for example).

PRIOR ART DOCUMENTS

Patent Documents

[Patent Document 1]
 Japanese Unexamined Patent Application Publication No. H11-325849
[Patent Document 2]
 Japanese Unexamined Patent Application Publication No. 2002-139421
[Patent Document 3]
 Japanese Unexamined Patent Application Publication No. 2007-24677
[Patent Document 4]
 Japanese Unexamined Patent Application Publication No. 2006-153838
[Patent Document 5]
 Japanese Unexamined Patent Application Publication No. 2008-73099
[Patent Document 6]
 Japanese Unexamined Patent Application Publication No. H09-276232

[Patent Document 7]
Japanese Unexamined Patent Application Publication No. 2008-259544
[Patent Document 8]
Japanese Unexamined Patent Application Publication No. 2010-88541
[Patent Document 9]
Japanese Unexamined Patent Application Publication No. 2008-272256
[Patent Document 10]
Japanese Unexamined Patent Application Publication No. 2011-24930
[Patent Document 11]
Japanese Unexamined Patent Application Publication No. 2011-72716

SUMMARY OF THE INVENTION

Problem that the Invention is to Solve

However, examination with a perimeter (referred to as perimetry, visual field test, etc.) takes time and is carried out in dark environment. Therefore, in the case in which a patient is an old person or tired, it is difficult to precisely carry out the examination. Moreover, burdens on a patient and examiner are large in perimetry.

On the other hand, although it is possible to intend to shorten examination time when OCT is used, it cannot be said that conventional technologies provide enough information for center management. Thus, center management cannot be carried out based on objective criteria for evaluation, and diagnosis depends greatly on proficiency of doctors.

The present invention is developed in order to solve such problems, and its purpose is to provide a fundus observation apparatus that obtains an image of an eye fundus by using optical coherence tomography (OCT) and a fundus image analyzing apparatus that are capable of providing objective data for center management while considering reduction of examination time.

Means for Solving the Problem

A fundus observation apparatus according to an embodiment includes: an optical system, image forming part, specifying part, association information generating part, evaluation information generating part. The optical system is configured to divide light from a light source into signal light and reference light, generate interference light by superposing the signal light having traveled by way of an eye fundus and the reference light having traveled by way of a reference optical path, and detect the interference light. The image forming part is configured to form a cross sectional image of the eye fundus based on detection results of the interference light. The specifying part is configured to analyze the cross sectional image to specify an abnormal region located in the vicinity of central fovea of the eye fundus. The association information generating part is configured to calculate the distance between the central fovea and the abnormal region and generate association information in which the direction of the abnormal region relative to the central fovea and the distance are associated with each other. The evaluation information generating part is configured to generate evaluation information for evaluating the state of the eye fundus based on the association information.

Effect of the Invention

According to the embodiment, evaluation information can be obtained based on the state of distribution of abnormal regions in the neighborhood of central fovea. By carrying out such examination instead of visual field test, it is possible to provide objective data for center management while considering reduction of examination time.

MODE FOR CARRYING OUT THE INVENTION

Examples of embodiments of the present invention will be described in detail with reference to the drawings. A fundus observation apparatus according to the present invention forms a cross sectional image (including at least one of a two-dimensional cross sectional image and three-dimensional image) of a fundus by using OCT. Further, a fundus image analyzing apparatus according to the present invention receives a cross sectional image of a fundus acquired by using OCT. Images obtained by OCT are sometimes referred to as OCT images. Furthermore, a measuring action for forming an OCT image is sometimes referred to as OCT measurement. It should be noted that the contents described in the documents cited in this description may be applied to the following embodiments.

In the following embodiments, configurations in which Fourier Domain OCT is employed will be described in detail. Particularly, fundus observation apparatuses according to the following embodiments are capable of obtaining both a fundus OCT image with Spectral Domain OCT and a fundus image, which is similar to the apparatus disclosed in Patent Document 4. It should be noted that configurations according to the present invention may be applied to a fundus observation apparatus of any type other than Spectral Domain (for example, Swept Source OCT). Further, apparatuses in which an OCT apparatus and a retinal camera are combined are explained in the embodiments; however, it is possible to combine an OCT apparatus comprising configuration according to the embodiments with a fundus imaging apparatus of any type, such as an SLO (Scanning Laser Ophthalmoscope), slit lamp microscope, ophthalmologic surgical microscope, etc. Further, configurations of the embodiment may be incorporated with a single-functional OCT apparatus.

[Configurations]

Figure 1:
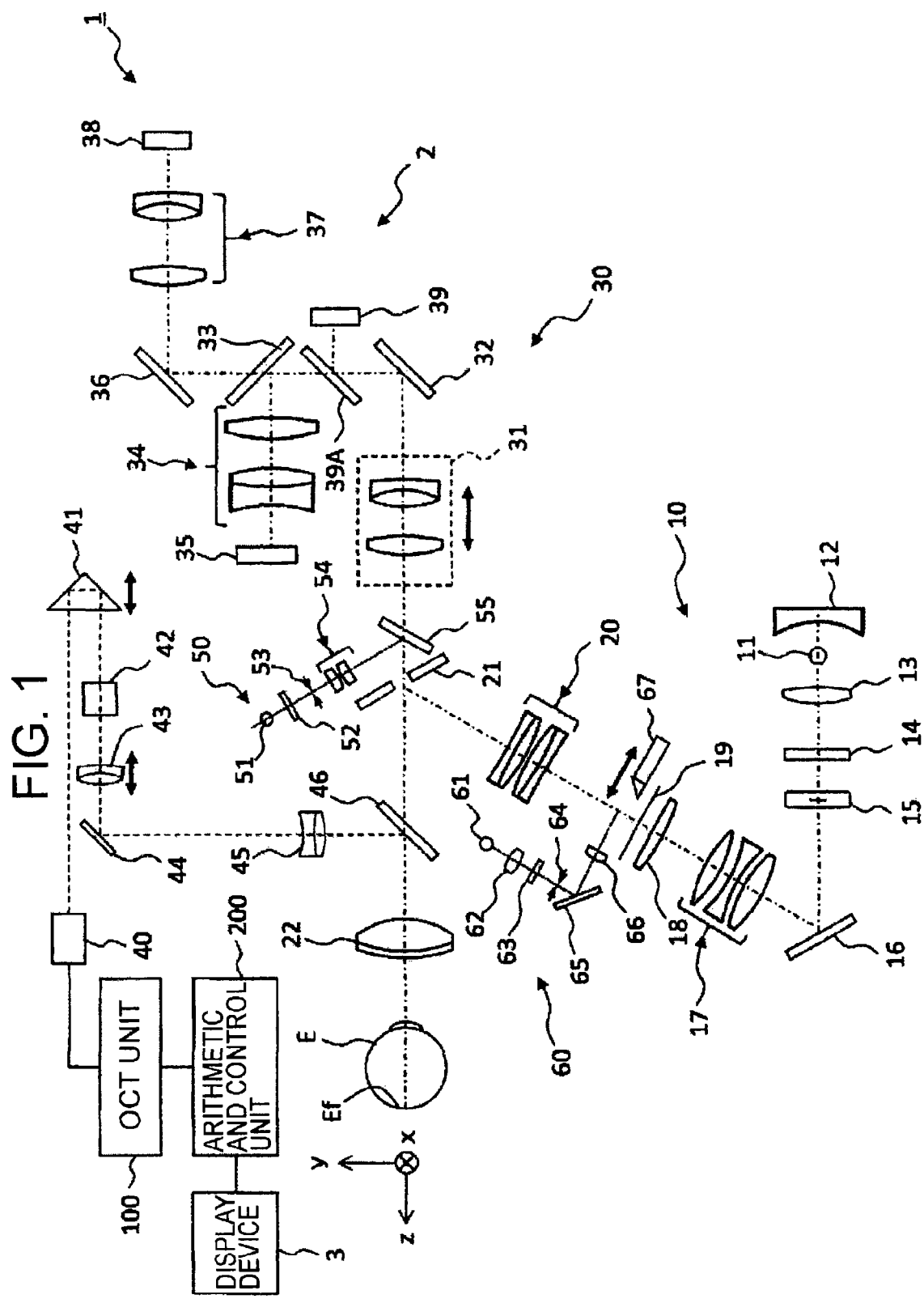
FIG. 1 is a schematic diagram showing an example of a configuration of a fundus observation apparatus according to an embodiment.
Figure 2:
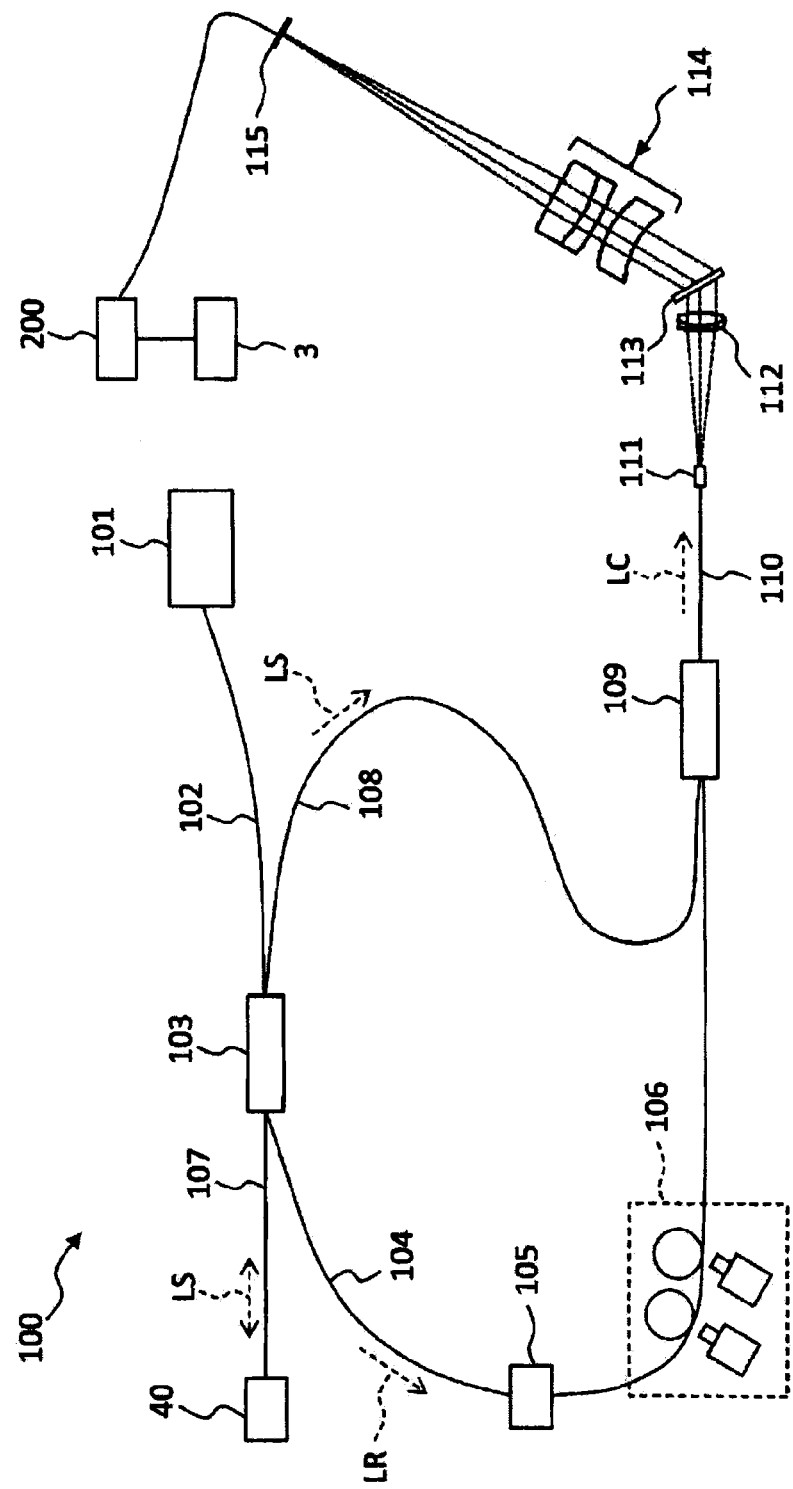
FIG. 2 is a schematic diagram showing an example of a configuration of a fundus observation apparatus according to an embodiment.

A fundus observation apparatus 1, as shown in FIG. 1 and FIG. 2, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on. The arithmetic and control unit 200 functions as "fundus image analyzing apparatus".

[Retinal Camera Unit]

The retinal camera unit 2 shown in FIG. 1 is provided with an optical system for forming a 2-dimensional image (fundus image) representing the surface morphology of the fundus Ef of an eye E. Fundus images include observation images, photographed images, etc. The observation image is, for example, a monochromatic moving image formed at a prescribed frame rate using near-infrared light. The photographed image may be, for example, a color image captured by flashing visible light, or a monochromatic still image captured by using near-infrared light or visible light as illumination light. The retinal camera unit 2 may also be configured to be capable of capturing other types of images such as a fluorescein angiography image, an indocyanine green fluorescent image, and an autofluorescent image. it should be noted that the retinal camera unit 2 is an example of "imaging part". Further, a fundus image acquired by the retinal camera unit 2 is an example of "surface image of eye fundus".

The retinal camera unit 2 is provided with a chin rest and a forehead placement for supporting the face of the subject. Moreover, the retinal camera unit 2 is provided with the illumination optical system 10 and the imaging optical system 30. The illumination optical system 10 irradiates illumination light to the fundus Ef. The imaging optical system 30 guides a fundus reflected light of the illumination light to imaging devices (CCD image sensors 35, 38 (sometimes referred to simply as CCD)). Moreover, the imaging optical system 30 guides signal light input from the OCT unit 100 to the fundus Ef, and guides the signal light returned from the fundus Ef to the OCT unit 100.

An observation light source 11 of the illumination optical system 10 comprises, for example, a halogen lamp. Light (observation illumination light) output from the observation light source 11 is reflected by a reflection mirror 12 with a curved reflection surface, and becomes near-infrared after passing through a visible cut filter 14 via a condenser lens 13. Furthermore, the observation illumination light is once converged near an imaging light source 15, reflected by a mirror 16, and passes through relay lenses 17 and 18, a diaphragm 19, and a relay lens 20. Then, the observation illumination light is reflected on the peripheral part (the surrounding region of an aperture part) of an aperture mirror 21, transmitted through a dichroic mirror 46, and refracted by an object lens 22, thereby illuminating the fundus Ef. It should be noted that LED (Light Emitting Diode) may be used as the observation light source.

The fundus reflection light of the observation illumination light is refracted by the object lens 22, transmitted through the dichroic mirror 46, passes through the aperture part formed in the center region of the aperture mirror 21, transmitted through a dichroic mirror 55, travels through a focusing lens 31, and reflected by a mirror 32. Furthermore, the fundus reflection light is transmitted through a half-mirror 39A, refracted by reflected by a dichroic mirror 33, and forms an image on the light receiving surface of the CCD image sensor 35 by a condenser lens 34. The CCD image sensor 35 detects the fundus reflection light at a preset frame rate, for example. An image (observation image) based on the fundus reflection light detected by the CCD image sensor 35 is displayed on a display device 3. It should be noted that when the imaging optical system is focused on the anterior eye part, the observation image of the anterior eye part of the eye E is displayed.

The imaging light source 15 comprises, for example, a xenon lamp. The light (imaging illumination light) output from the imaging light source 15 is irradiated to the fundus Ef via the same route as that of the observation illumination light. The fundus reflection light of the imaging illumination light is guided to the dichroic mirror 33 via the same route as that of the observation illumination light, transmitted through the dichroic mirror 33, reflected by a mirror 36, and forms an image on the light receiving surface of the CCD image sensor 38 by a condenser lens 37. An image (photographed image) based on the fundus reflection light detected by the CCD image sensor 38 is displayed on the display device 3. It should be noted that the display device 3 for displaying the observation image and the display device 3 for displaying the photographed image may be the same or different. Further, when similar photographing is carried out by illuminating the eye E with infrared light, infrared photographed image is displayed. Moreover, LED may be used as the imaging light source.

An LCD (Liquid Crystal Display) 39 displays a fixation target or a target for measuring visual acuity. The fixation target is a visual target for fixating the eye E, and is used when photographing a fundus or performing OCT measurement.

Part of the light output from the LCD 39 is reflected by the half-mirror 39A, reflected by the mirror 32, passes through the aperture part of the aperture mirror 21, refracted by the object lens 22, and projected onto the fundus Ef.

By changing a display position of the fixation target on the screen of the LCD 39, it is possible to change the fixation position of the eye E. Examples of the fixation positions of the eye E include the position for acquiring an image centered at the macula of the fundus Ef, the position for acquiring an image centered at the optic papilla, the position for acquiring an image centered at the fundus center located between the macula and the optic papilla, and so on, as in conventional retinal cameras. Further, the display position of the fixation target may be arbitrarily changed.

Furthermore, as with conventional retinal cameras, the retinal camera unit 2 is provided with an alignment optical system 50 and a focus optical system 60. The alignment optical system 50 generates a target (alignment target) for matching the position (alignment) of the device optical system with respect to the eye E. The focus optical system 60 generates a target (split target) for matching the focus with respect to the eye Ef.

Light (alignment light) output from an LED 51 of the alignment optical system 50 passes through diaphragms 52 and 53 and a relay lens 54, is reflected by the dichroic mirror 55, passes through the aperture part of the aperture mirror 21, is transmitted through the dichroic mirror 46, and is projected onto the cornea of the eye E by the object lens 22.

Cornea reflection light of the alignment light passes through the object lens 22, the dichroic mirror 46 and the aperture part, a part of the cornea reflection light is transmitted through the dichroic mirror 55, passes through the focusing lens 31, reflected by the mirror 32, transmitted through the half-mirror 39A, reflected by the dichroic mirror 33, and projected onto the light receiving surface of the CCD image sensor 35 by the condenser lens 34. An image (alignment target) captured by the CCD image sensor 35 is displayed on the display device 3 together with the observation image. The user conducts alignment by an operation that is the same as conventional retinal cameras. Further, alignment may be performed in a way in which the arithmetic and control unit 200 analyzes the position of the alignment target and controls the movement of the optical system (automatic alignment function).

In order to conduct focus adjustment, the reflection surface of a reflection rod 67 is positioned at a slanted position on the optical path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light passes through the relay lens 20, is reflected at the aperture mirror 21, is transmitted through the dichroic mirror 46, is refracted by the object lens 22, and is projected onto the fundus Ef.

The fundus reflection light of the focus light passes through the same route as the cornea reflection light of the alignment light and is detected by the CCD image sensor 35. An image (split target) captured by the CCD image sensor 35 is displayed on the display device 3 together with the observation image. The arithmetic and control unit 200, as in the conventional technology, analyzes the position of the split target, and moves the focusing lens 31 and the focus optical system 60 for focusing (automatic focusing function). Further, focusing may be performed manually while visually recognizing the split target.

The dichroic mirror 46 splits the optical path for OCT from the optical for eye fundus photographing. The dichroic mirror 46 reflects light of the wavelength band used for OCT, and transmits the light for eye fundus photographing. The optical path for OCT is provided with a collimator lens unit 40, an optical path length changing part 41, a galvano scanner 42, a focusing lens 43, a mirror 44 and a relay lens 45.

The optical path length changing part 41 is capable of moving in the direction indicated by the arrow in FIG. 1 to change the length of the optical path for OCT. This change of optical path length may be used for correction of the optical path length in accordance with the axial length of the eye E, and for adjustment of the condition of interference. The optical path length changing part 41 is configured to comprise a corner cube and a mechanism for moving the corner cube, for example.

The galvano scanner 42 changes the travelling direction of light (signal light LS) travelling along the optical path for OCT. Thereby, the fundus Ef is scanned by the signal light LS. The galvano scanner 42 is configured to comprise a galvano mirror for scanning with the signal light LS in the x-direction, a galvano mirror for scanning in the y-direction, and a mechanism for independently driving these. Thereby, the signal light LS may be scanned in an arbitrary direction in the xy-plane.

[OCT Unit]

An example of the configuration of the OCT unit 100 is explained while referring to FIG. 2. The OCT unit 100 is provided with an optical system for obtaining an OCT image of the fundus Ef. The optical system comprises a similar configuration to a conventional Spectral Domain OCT apparatus. That is to say, this optical system is configured to split low-coherence light into signal light and reference light, superpose the signal light returned form the fundus Ef and the reference light having traveled through a reference optical path to generate interference light, and detect the spectral components of the interference light. This detection result (detection signal) is transmitted to the arithmetic and control unit 200.

It should be noted that when Swept Source OCT apparatus is used, a swept source is provided instead of a low-coherence light source while an optical member for spectrally decomposing interference light is not provided. In general, any known technology in accordance with the type of OCT may be arbitrarily applied for the configuration of the OCT unit 100.

A light source unit 101 outputs broadband low-coherence light L0. The low-coherence light L0, for example, includes near-infrared wavelength band (about 800-900 nm) and has a coherence length of about tens of micrometer. Moreover, it is possible to use, as the low-coherence light L0, near-infrared light having wavelength band that is impossible to be detected by human eyes, for example, infrared light having the center wavelength of about 1040-1060 nm.

The light source unit 101 is configured to comprise light output device, such as an SLD (super luminescent diode), LED, SOA (Semiconductor Optical Amplifier) and the like.

The low-coherence light L0 output from the light source unit 101 is guided to a fiber coupler 103 by an optical fiber 102 and split into the signal light LS and the reference light LR.

The reference light LR is guided to an optical attenuator 105 by an optical fiber 104. Through any known technology, the optical attenuator 105 received control of the arithmetic and control unit 200 for automatically adjusting light amount (light intensity) of the reference light LR guided to the optical fiber 104. The reference light LR having adjusted by the optical attenuator 105 is guided to a polarization controller 106 by the optical fiber 104. The polarization controller 106 is a device configured to, for example, apply stress to the loop-form optical fiber 104 from outside to adjust polarization condition of the reference light LR being guided in the optical fiber 104. It should be noted that the configuration of the polarization controller 106 is not limited to this, and arbitrary known technology may be applied. The reference light LR having adjusted by the polarization controller 106 is guided to an optical coupler 109.

The signal light LS generated by the fiber coupler 103 is guided by the optical fiber 107, and converted into a parallel light flux by the collimator lens unit 40. Further, the signal light LS travels through the optical path length changing part 41, the galvano scanner 42, the focusing lens 43, the mirror 44 and the relay lens 45, and reaches the dichroic mirror 46. Further, the signal light LS is reflected by the dichroic mirror 46, refracted by the objective lens 22, and projected to the fundus Ef. The signal light LS is scattered (including reflection) at various depth positions of the fundus Ef. The back-scattered light of the signal light LS from the fundus Ef travels along the same route as the outward way in the opposite direction to the fiber coupler 103, and is reached the fiber coupler 109 through an optical fiber 108.

The fiber coupler 109 superposes the back-scattered light of the signal light LS and the reference light LR having passed through the optical fiber 104. Interference light LC thus generated is guided by an optical fiber 110 and output from an exit end 111. Furthermore, the interference light LC is converted into a parallel light flux by a collimator lens 112, spectrally divided (spectrally decomposed) by a diffraction grating 113, converged by a condenser lens 114, and projected onto the light receiving surface of a CCD image sensor 115. It should be noted that although the diffraction grating 113 shown in FIG. 2 is of transmission type, any other kind of a spectrally decomposing element (such as reflection type) may be used.

The CCD image sensor 115 is for example a line sensor, and detects the respective spectral components of the spectrally decomposed interference light LC and converts the components into electric charges. The CCD image sensor 115 accumulates these electric charges, generates a detection signal, and transmits the detection signal to the arithmetic and control unit 200.

Although a Michelson-type interferometer is employed in the present embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, may be used.

[Arithmetic and Control Unit]

A configuration of the arithmetic and control unit 200 will be described. The arithmetic and control unit 200 analyzes the detection signals input from the CCD image sensor 115 to form an OCT image of the fundus Ef. Arithmetic processing for this may be the same as that of a conventional Spectral Domain OCT apparatus.

Further, the arithmetic and control unit 200 controls each part of the retinal camera unit 2, the display device 3 and the OCT unit 100. For example, the arithmetic and control unit 200 displays an OCT image of the fundus Ef on the display device 3.

Further, as controls of the retinal camera unit 2, the arithmetic and control unit 200 executes: controls of actions of the observation light source 101, the imaging light source 103 and LED's 51 and 61; control of action of the LCD 39; controls of movements of the focusing lenses 31 and 43; control of movement of the reflection rod 67; control of movement of the focus optical system 60; control of movement of the optical path length changing part 41; control of action of the galvano scanner 42; and so on.

Further, as controls of the OCT unit 100, the arithmetic and control unit 200 executes: control of action of the light source unit 101; control of action of the optical attenuator 105; control of action of the polarization controller 106; control of action of the CCD image sensor 115; and so on.

The arithmetic and control unit 200 comprises a microprocessor, a RAM, a ROM, a hard disk drive, a communication interface, and so on, as in conventional computers. The storage device such as the hard disk drive stores a computer program for controlling the fundus observation apparatus 1. The arithmetic and control unit 200 may be provided with various circuit boards such as a circuit board for forming OCT images. Moreover, the arithmetic and control unit 200 may be provided with operation devices (input devices) such as a keyboard, a mouse, etc. and/or a display device such as an LCD etc.

The retinal camera unit 2, the display device 3, the OCT unit 100, and the arithmetic and control unit 200 may be integrally configured (that is, provided within a single case), or separately configured in two or more cases.

[Control System]

Figure 3:
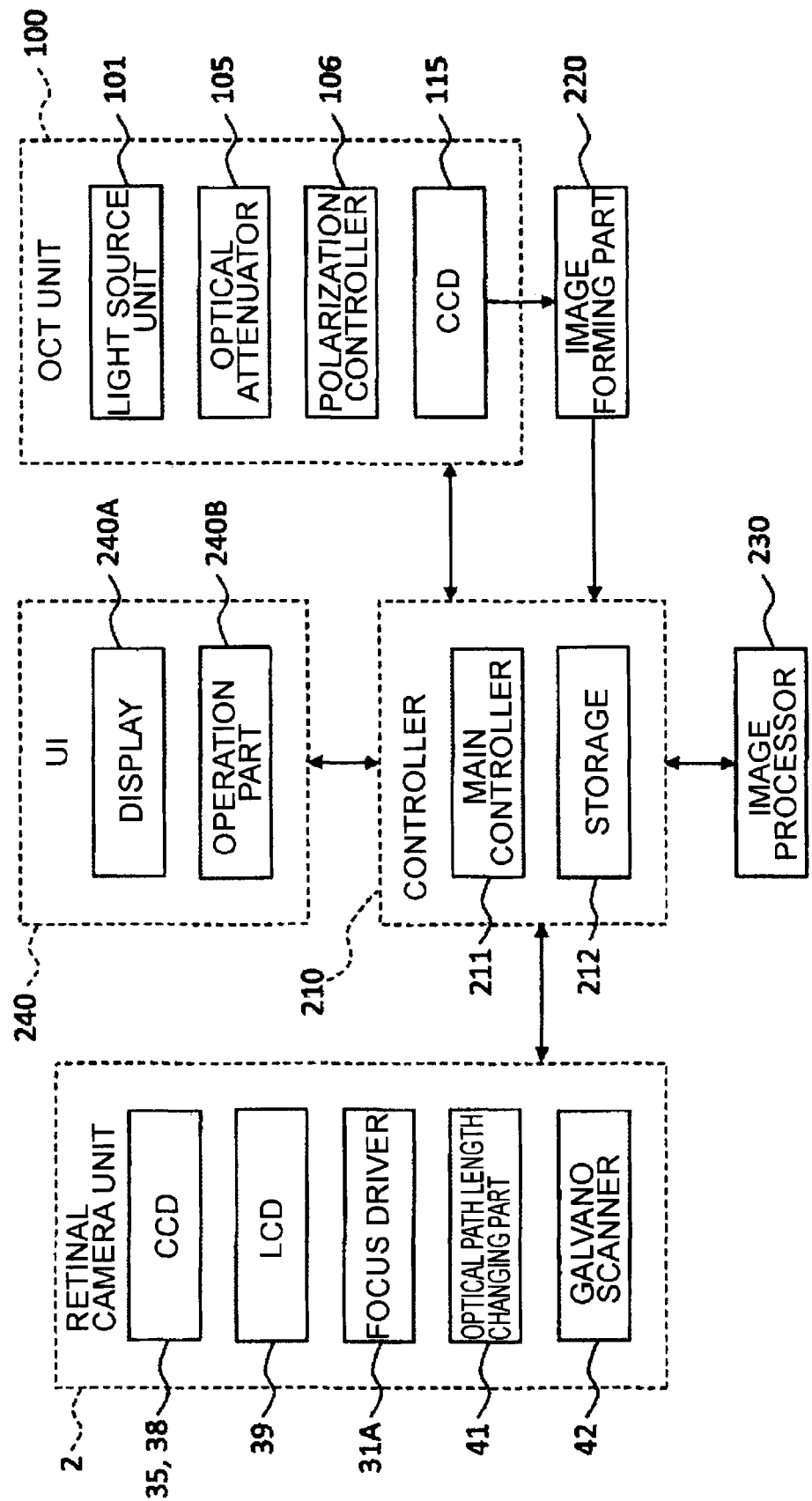
FIG. 3 is a schematic block diagram showing an example of a configuration of a fundus observation apparatus according to an embodiment.
Figure 4:
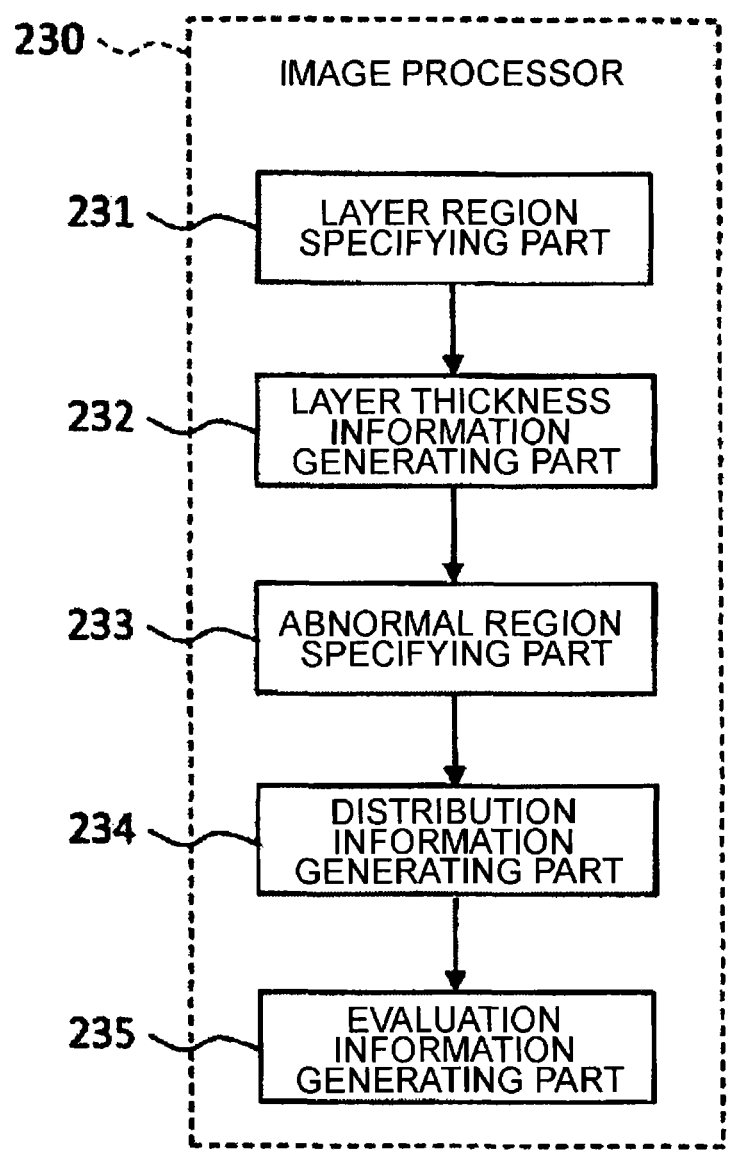
FIG. 4 is a schematic block diagram showing an example of a configuration of a fundus observation apparatus according to an embodiment.

A configuration of a control system of the fundus observation apparatus 1 will be described with reference to FIGS. 3 and 4.

(Controller)

The control system of the fundus observation apparatus has a configuration centered on a controller 210 The controller 210 is configured to comprise, for example, the aforementioned microprocessor, RAM, ROM, hard disk drive, and communication interface, etc. The controller 210 is provided with a main controller 211 and storage 212.

(Main Controller)

The main controller 211 performs the aforementioned various kinds of controls. Specifically, the main controller 211 controls a focus driver 31A, the optical path length changing part 41 and the galvano scanner 42 of the retinal camera unit 2, and further controls the light source unit 101, the optical attenuator 105 and the polarization controller 106 of the OCT unit 100. Further, the main controller 211 executes various display controls as described later. The main controller 211 functions as an example of "display controller".

The focus driver 31A moves the focusing lens 31 in the direction of the optical axis. Thereby, the focus position of the imaging optical system 30 is changed. It should be noted that the main controller 211 may control an optical system driver (not shown in diagrams) to three dimensionally move the optical system provided in the retinal camera unit 2. This control is used for alignment and tracking. Tracking is an operation for move the optical system in accordance with eye movement of the eye E. When tracking is applied, alignment and focusing are carried out in advance. Tracking is a function to maintain adequate positional relationship in which alignment and focusing are matched by causing the position of the optical system to follow the eye movement.

The main controller 211 executes a process of writing data into the storage 212, and a process of reading out data from the storage 212.

(Storage)

The storage 212 stores various kinds of data. The data stored in the storage 212 may include image data of OCT images, image data of fundus images, and eye information, for example. The eye information includes information on the eye, such as information on a subject such as a patient ID and a name, identification information on left eye or right eye, and so on. Further, the storage 212 stores various programs and data for operating the fundus observation apparatus 1.

(Image Forming Part)

An image forming part 220 forms image data of a cross sectional image of the fundus Ef based on the detection signals from the CCD image sensor 115. Like conventional Spectral Domain OCT, this process includes processes such as noise elimination (noise reduction), filtering and FFT (Fast Fourier Transform). In the case in which other OCT type is applied, the image forming part 220 executes known process in accordance with the applied OCT type. The image forming part 220 functions as "image forming part". It should be noted that when a three-dimensional image of the fundus Ef is analyzed, the image forming part 220 and the image processor 230 (that is, a function to form a three-dimensional image) correspond to "image forming part".

The image forming part 220 comprises the aforementioned circuit board, for example. It should be noted "image data" and the "image" based on the image data may be identified with each other in the description. Further, a site of the fundus Ef and an image thereof may be identified with each other.

(Image Processor)

An image processor 230 executes various image processing and analysis processing on images formed by the image forming part 220. For example, the image processor 230 executes various correction processing such as brightness correction, dispersion correction of images, etc. Further, the image processor 230 executes various image processing and analysis processing on images obtained by the retinal camera unit 2 (fundus images, anterior eye part images, etc.).

The image processor 230 executes known image processing such as interpolation processing for interpolating pixels between cross sectional images to form image data of a three-dimensional image of the fundus Ef. It should be noted that the image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process (such as volume rendering and MIP (Maximum Intensity Projection)) on this volume data, and forms image data of a pseudo three-dimensional image taken from a specific view direction. On a display device such as a display 240A, this pseudo three-dimensional image is displayed.

Further, it is also possible to form stack data of multiple cross sectional images as the image data of a three-dimensional image. Stack data is image data obtained by three-dimensionally arranging multiple cross sectional images obtained along multiple scanning lines, based on the positional relation of the scanning lines. That is to say, stack data is image data obtained by expressing multiple cross sectional images defined by originally individual two-dimensional coordinate systems by a three-dimensional coordinate system (in other words, embedding into a three-dimensional space).

The image processor 230 may carry out position matching (registration) between a fundus image and an OCT image. When a fundus image and an OCT image are acquired in parallel, since both optical systems are coaxial, the fundus image and the OCT image which are acquired (substantially) in parallel can be matched by considering the optical axis of the imaging optical system 30 as a reference. Further, regardless of acquisition timings of a fundus image and an OCT image, it is possible to match an image obtained by projecting the OCT image onto the xy-plane with the fundus image, thereby matching the OCT image and the fundus image.

The image processor 230 comprises a layer region specifying part 231, layer thickness information generating part 232, abnormal region specifying part 233, distribution information generating part 234 and evaluation information generating part 235. Here, the layer region specifying part 231, layer thickness information generating part 232 and abnormal region specifying part 233 function as an example of "specifying part". Further, the distribution information generating part 234 functions as an example of "association information generating part".

(Layer Region Specifying Part)

The layer region specifying part 231 is configured to analyze a cross sectional image of the fundus Ef to specify a layer region. This cross sectional image may be two-dimensional cross sectional image or three-dimensional image. The layer region means an image region in the cross sectional image that corresponds to a stratiform (or membranous) tissue(s) existing in the fundus Ef. It should be noted that there are a retina, choroid and sclera in the fundus Ef. The retina may be histologically classified into ten layers, namely, a retinal pigment epithelium layer, visual cell layer, outer limiting membrane, outer granular layer, outer plexiform layer, inner granular layer, inner plexiform layer, ganglion cell layer, nerve fiber layer and inner limiting membrane in this order from the outside. The layer region may be an image region corresponding to one or more tissues in the fundus Ef having such structure.

The layer region specifying part 231 can specify a layer region based on pixel values (brightness value) of the cross sectional image. Further, the layer region specifying part 231 may be configured to specify multiple layer regions based on pixel values of the cross sectional image and select a layer region based on the pixel values, shape etc. thereof. Alternatively, the layer region specifying part 231 may be configured to specify a characteristic site of the fundus Ef (for example, surface of retina, layer region having characteristic pixel values) and specify a layer region based on distance from the characteristic site. In general, specification of a layer region may be carried out by using arbitrary known technology (image processing technology).

(Layer Thickness Information Generating Part)

The layer thickness information generating part 232 is configured to analyze the layer region specified by the layer region specifying part 231 to generate layer thickness information related to thickness of this layer region. Examples of the layer thickness information include thickness distribution information, symmetric position information, both-eye information. It should be noted that kinds of the layer thickness information are not limited to these. Further, the layer thickness information includes at least one of multiple information including these.

The thickness distribution information represents distribution of the thickness of the layer region in the cross section of the fundus Ef represented by the cross sectional image of the fundus Ef. As an example of processing for generating this information, the layer thickness information generating part 232 obtains thickness of a preset layer (that is, distance along the z-direction between the upper and lower surfaces of this layer) at an arbitrary location in the cross section (that is, location at arbitrary xy-coordinates), and associates the location and the thickness. The thickness of the layer may be calculated by counting the number of pixels arranged in the z-direction wherein the pixels compose the layer region, or by calculating distance in the real space defined for the cross sectional image.

The symmetric position information represents difference or ratio of the thicknesses of the layer region at symmetric positions with respect to central fovea of the fundus Ef. The central fovea (that is, the image position corresponding to the central fovea) may be identified as the deepest part or the center of the hollow of macula area depicted in the cross sectional image, may be identified as the center position of the macular area specified based on the pixel values of the fundus image, may be identified from scan position information by the galvano scanner 42, or may be identified based on the positional relationship between fixation position and the axis of optical system (that is, center position of a frame). Instead of identifying by using image analysis, the central fovea may be input manually onto a displayed image of the fundus image or cross sectional image. Further, in the case in which fundus images and/or cross sectional images of the eye E acquired in the past can be referred to, it is possible to identify the location of the central fovea in the current image based on the location of the central fovea identified based on this past image and positional relationship between the past image and the current image. The positional relationship in this process is obtained, for example, by registration between images based on characteristic points (macular area, optic papilla, characteristic blood vessel, branch point of blood vessel, etc.) in the past image and the concerned characteristic points in the current image.

The symmetric positions with respect to central fovea are two positions which are point symmetrical with respect to the central fovea, for example. These two point symmetrical positions are two positions which are away from the central fovea by an equal distance on a line segment passing through the central fovea. The distance from the central fovea may be specified as the number of pixels, or may be specified as distance in the real space defined for the xy-plane. Other examples of the symmetrical positions may include two positions which are linear symmetrical with respect to a line passing through the central fovea.

The thicknesses at such two positions are calculated in the same fashion as the thickness distribution information. The layer thickness information generating part 232 calculates difference or ratio of two thickness values at a pair of symmetrical positions. When calculating difference, the difference may be obtained by subtracting one thickness value from the other thickness value, or may be obtained by calculating the absolute value of the difference. It should be noted that the calculated value may be negative in the former case. When calculating ratio, the ratio may be calculated by assigning one thickness value to a denominator and the other to a numerator based on a preset orientation.

The both-eye information is applied to the case in which a cross sectional image is formed for each of right and left eyes of one patient. The both-eye information represents difference or ratio of the thicknesses of the layer regions at symmetric positions between the fundus of the right eye and the fundus of the left eye. The symmetric positions are positions in which vertical position is defined as upward and downward directions for both eyes and horizontal position is defined as nose and ear directions. In other words, the symmetric positions are mirror-image positions with respect to a body axis (or center line of a face), that is, symmetrical positions in mirror images. The method of calculating the thickness at respective positions and the method of calculating difference or ratio may be same as the abovementioned methods.

(Abnormal Region Specifying Part)

The abnormal region specifying part 233 is configured to specify an abnormal region based on the layer thickness information generated by the layer thickness information generating part 232. The abnormal region may include not only a region judged as a site in which abnormality of the fundus Ef has been actually caused by a disease but also a region presumed to be a site in which abnormality may have been caused.

In the present embodiment, an evaluation target is the thickness of a layer region (that is, becoming thinner or becoming thicker). Evaluation of the thickness of a layer region may be carried out, for example, by comparing with a normal range that is set based on a statistic (mean value, standard deviation, etc.) of thicknesses acquired from OCT measurements of multiple normal eyes. This normal range may be constant over a whole measurement target region, or may be set for each of multiple regions obtained from dividing the measurement target region. Further, the normal region may be set individually for respective layer regions.

The abnormality to be judged is not limited to structural abnormalities, and it may be functional abnormalities such as blood flow or optical abnormalities. Type of OCT images to which analysis processing is applied is determined according to type of such abnormalities. For example, ordinary OCT images that depict morphology of the fundus Ef is applied when structural abnormality is judged, OCT images acquired from functional measurement (Doppler OCT etc.) is applied when functional abnormality is judged, and OCT images acquired from optical characteristic measurement (polarization OCT etc.) is applied when optical abnormality is judged.

There are cases in which noises are mixed in OCT images. In order to eliminate influence of noises, processing for specifying an abnormal region may include processes of: calculating the size of a region that is provisionally specified to be abnormal; and judging this (provisional) abnormal region as a normal region when the size thereof is equal to or less than a preset threshold. This size (area, volume, etc.) may be calculated as the number of pixels included in the abnormal region, or may be calculated as the size in the real space. Further, the threshold can be obtained in an arbitrary manner; for example, the size of noises may be calculated by actually carrying out OCT measurement, may be calculated theoretically, or may be calculated from clinical data of sizes of abnormalities.

(Distribution Information Generating Part)

In the present embodiment, multiple cross sectional images of multiple cross sections located in the vicinity of the central fovea to the fundus Ef are acquired, and analysis processing is applied to these cross sectional images. For this purpose, the fundus observation apparatus 1 sets fixation position for macula and carries out radial scan described below. This radial scan comprises a preset number of linear scans (line scans) that are centered at central fovea, for example. These linear scans are arranged at intervals of an equal angle. The number of linear scans is arbitrary set; larger number (for example, 180 linear scans at 1 degree intervals) is set when intending to improving precision of examination, and smaller number is set when intending to shorten examination time. It should be noted that a scanning mode that is applicable in the present embodiment is not limited to the radial scan, and it is possible to apply other scanning modes such as three-dimensional scan.

The distribution information generating part 234 analyzes a cross sectional image corresponding to each of the line scans to calculate the distance between the central fovea and the abnormal region in the concerned cross section. This cross section is a plane that is along the locus of a line scan and spreads in the z-direction. Further, processing of calculating distance comprises specification of an abnormal region in the concerned cross section. More specifically, the distribution information generating part 234 identifies xy-coordinates common between the abnormal region specified by the abnormal region specifying part 233 and the concerned cross section, and selects, from among the xy-coordinates identified, xy-coordinates that is closest to the xy-coordinates of the central fovea. The distance between the selected xy-coordinates and the xy-coordinates of the central fovea is regarded as the distance between the central fovea and the abnormal region in the concerned cross section. It should be noted that there is no abnormal region in the concerned cross section when there is no common xy-coordinates. Further, this distance may be expressed as the number of pixels or distance in the real space in the same way as calculation of thickness of a layer region described above.

The distribution information generating part 234 carries out the above calculation processing on each of the cross sectional images. Thereby, distribution information that represents distribution of distances in multiple directions corresponding to the multiple cross sections. The multiple directions corresponding to the multiple cross sections may be direction defined by setting the central fovea as a reference. In the present embodiment, the directions are defined such that angle 0 degree is set to a preset direction (x-axis direction, y-axis direction, etc.) and the value of angle increases in a preset rotation direction (clockwise direction or counterclockwise direction) in the xy-coordinate system with the origin located at central fovea. The distribution information is generated by associating the distance between central fovea and an abnormal region with each direction (angle etc.) defined in such a way. The distribution information is an example of "association information". Further, the distribution information generating part 234 functions as an example of "association information generating part".

Figure 5:
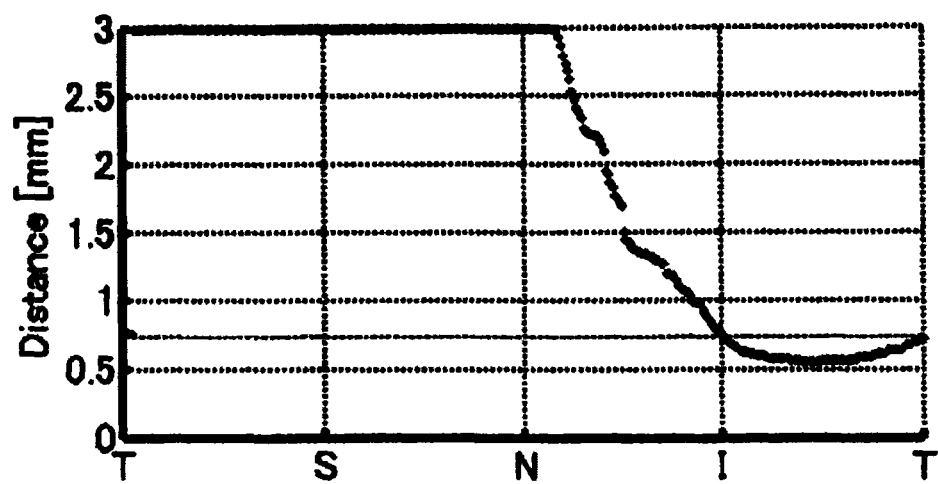
FIG. 5 is a schematic diagram for explaining an operation of a fundus observation apparatus according to an embodiment.

FIG. 5 illustrates an example of the distribution information. In this graph information, the horizontal axis shows direction in which central fovea is set to be the origin, and the vertical axis shows distance from the central fovea. "T", "S", "N" and "I" respectively shows temporal direction, superior direction, nasal direction and inferior direction, as conventionally used in ophthalmology. The angle between two neighboring directions is 90 a right angle. Further, an OCT measurement region corresponding to this graph information is a disc-shaped region of area that extends 3 mm in the respective directions from central fovea. Such OCT measurement is realized by radial scan that is a combination of multiple line scans of length 6 mm. Further, data included in the disk-shaped region may be extracted from data acquired by carrying out three-dimensional scan of 6 mm×6 mm area centered at central fovea. Further, concentric scan may be applied.

It can be seen from the graph information shown in FIG. 5 that there is no abnormal region from the temporal side to a location slightly beyond the nasal side via the superior side. In other words, it can be seen that there is no abnormal region in the upper semicircle region of the disk-shaped region. Moreover, distance between the abnormal region and central fovea is becoming gradually smaller from the location slightly beyond the nasal side toward the inferior side, and the distance becomes smallest at a location near the middle between the inferior side and the temporal side. Then, the distance between the abnormal region and central fovea is becoming gradually larger from this closest direction toward the temporal side.

The graph information is generated by the evaluation information generating part 235, for example. It should be noted that a template of a coordinate system for generating graph information is stored in the storage 212 etc. in advance. Graph information may be displayed on the display 240A by the main controller 211. In this case, the main controller 211 functions as "display controller". Graph information is an example of evaluation information described below.

Figure 6:
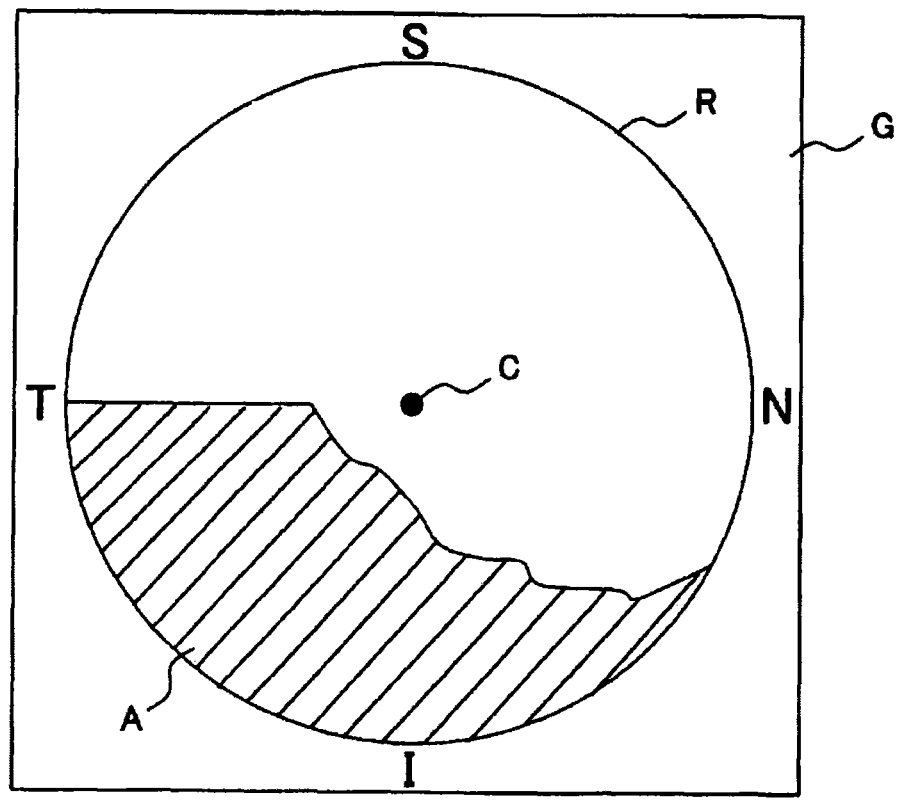
FIG. 6 is a schematic diagram for explaining an operation of a fundus observation apparatus according to an embodiment.

FIG. 6 illustrates distribution of abnormal regions that are the base of the graph information illustrated in FIG. 5. It should be noted that information that expresses the distribution of the abnormal regions (abnormal region distribution image) is formed based on distribution information and fundus image. The background of the abnormal region distribution image is a fundus image G photographed by the retinal camera unit 2. The fundus image G is photographed with fixation position for macula as described above, and central fovea C is depicted at almost center position of the frame. Here, the fundus image G may be an image obtained by trimming a wide-angle image, or may be an image photographed with an angle of view corresponding to the size of the scanning region R (disk-shaped region of a diameter 6 mm in this case). A shaded region shown by symbol A indicates an abnormal region. The abnormal region A is displayed in a different aspect from other regions (including normal regions). As an example of this, it is possible to assign a preset color to the partial region of the fundus image G corresponding to the abnormal region A, or to display the contour of this partial region.

The abnormal region distribution image is generated by the evaluation information generating part 235, for example. The abnormal region distribution image may be displayed on the display 240A by the main controller 211. In this case, the main controller 211 functions as "display controller". The abnormal region distribution image is an example of evaluation information described below.

(Evaluation Information Generating Part)

The evaluation information generating part 235 is configured to generate evaluation information used for diagnosis of the eye E based on the distribution information generated by the distribution information generating part 234. Items recorded as evaluation information is appropriately determined according to purpose of diagnosis. The evaluation information is displayed in a preset form by the main controller 211. Examples of the display modes include a method of displaying the evaluation information as a numerical value, a method of displaying the evaluation information as an image, and a method of displaying the evaluation information using graph information, and so on. Examples of evaluation information and display mode thereof are described below.

(First Example of Evaluation Information)

A first example of evaluation information includes information (nearest direction information) that expresses the direction in which an abnormal region is located nearest to central fovea. In order to achieve this, the evaluation information generating part 235 firstly compares the magnitudes of distances included in the distribution information generated by the distribution information generating part 234 to specify the minimum. Next, the evaluation information generating part 235 specifies the direction (nearest direction)

corresponding to this minimum by referring to the distribution information. Then, the evaluation information generating part 235 generates nearest direction information based on the nearest direction specified.

Figure 7:
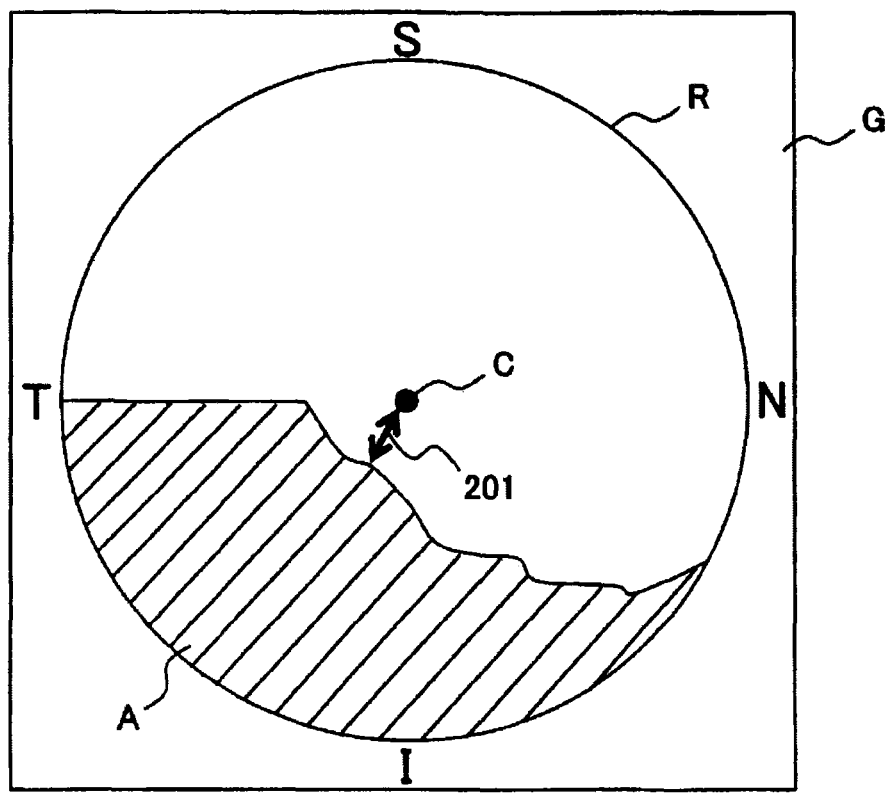
FIG. 7 is a schematic diagram for explaining an operation of a fundus observation apparatus according to an embodiment.
Figure 8:
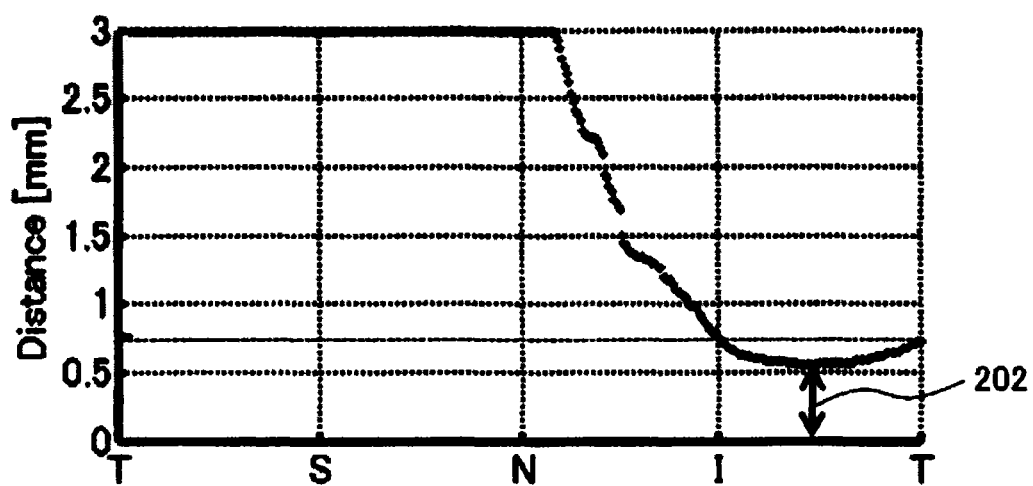
FIG. 8 is a schematic diagram for explaining an operation of a fundus observation apparatus according to an embodiment.

FIGS. 7 and 8 illustrate examples of the nearest direction information. In the example illustrated in FIG. 7, an arrow 201 that connects the central fovea C and the location on the abnormal region closest to the central fovea C is displayed, as evaluation information, on the abnormal region distribution image illustrated in FIG. 6. The direction shown by the arrow 201 indicates the nearest direction. Further, in the example illustrated in FIG. 8, an arrow 202 that indicates the position showing the nearest direction on the horizontal axis and the position on the graph nearest to the horizontal axis is displayed, as evaluation information, on the graph information illustrated in FIG. 5. It should be noted that the numerical value (that is, angle) indicating the nearest direction may be displayed together with the arrows 201 or 202.

It should be noted that, instead of selecting one nearest direction, it is possible to select certain number of directions from the nearest distance between the abnormal region and central fovea in order, and regard these as evaluation information. Similarity applies to display mode thereof.

(Second Example of Evaluation Information)

A second example of evaluation information is information (near direction information) that expresses direction in which the distance between abnormal region and central fovea is equal to or less than a preset threshold. In order to obtain the near direction information, the evaluation information generating part 235 firstly compares respective distances included in the distribution information with the preset threshold to select distances that are equal to or less than this threshold. This threshold may be a default setting, or may be arbitrarily set by a user. Next, the evaluation information generating part 235 specifies the direction corresponding to each of the selected directions by referring to the distribution information. Then, the evaluation information generating part 235 generates near direction information based on the direction specified.

Examples of the near direction information include the following:

(1) ratio information that expresses the ratio of directions in which the distance between a central fovea and abnormal region is equal to or less than a threshold;
(2) size information that expresses the size of normal region located between an abnormal region and central fovea in the direction in which the distance between a central fovea and abnormal region is equal to or less than a threshold; and
(3) a statistic of the thickness of an arbitrary layer region in this normal region.

The ratio information in the example (1) is explained. As described above, the ratio information expresses the ratio of directions in which the distance between a central fovea and abnormal region is equal to or less than a threshold. The ratio information is not limited to a ratio of such directions to the whole, and may be the number (or angles) of such directions. This is because the whole number and angle are determined in advance.

When ratio information is generated, the evaluation information generating part 235 firstly compares respective distances included in the distribution information with a threshold to specify distances that are equal to or less than this threshold. Next, the evaluation information generating part 235 specifies the direction corresponding to each of the specified directions by referring to the distribution information. Then, the evaluation information generating part 235 generates ratio information based on all the directions included in the distribution information and the specified direction. In this processing, a quotient or ratio may be calculated based on the number of the specified directions and the number of all the directions, or the number of the specified directions may be counted, for example.

Figure 9:
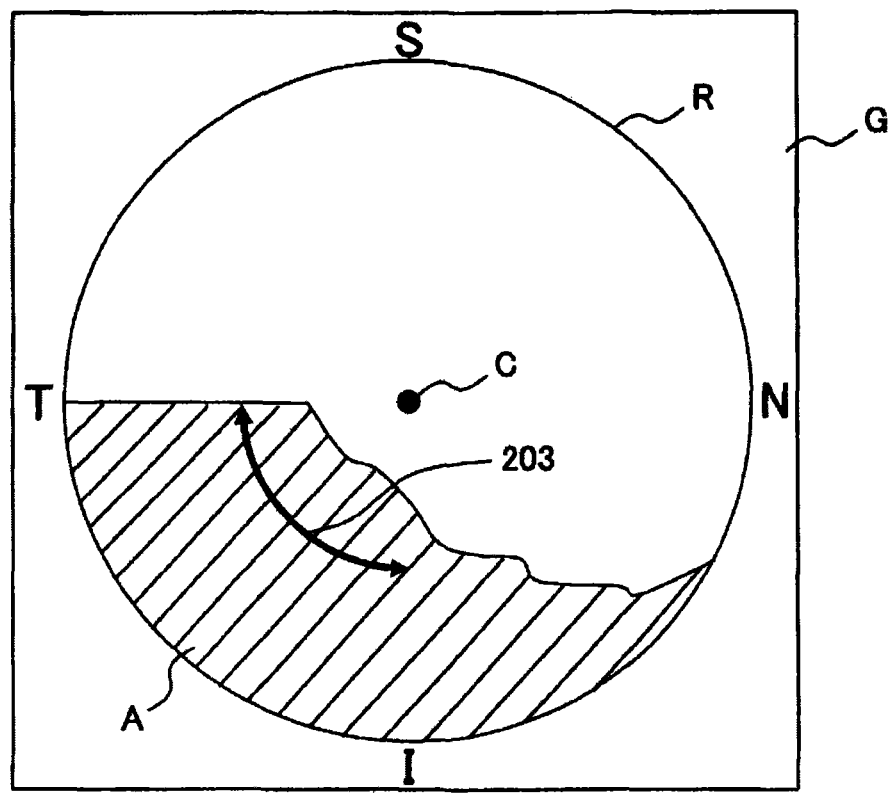
FIG. 9 is a schematic diagram for explaining an operation of a fundus observation apparatus according to an embodiment.
Figure 10:
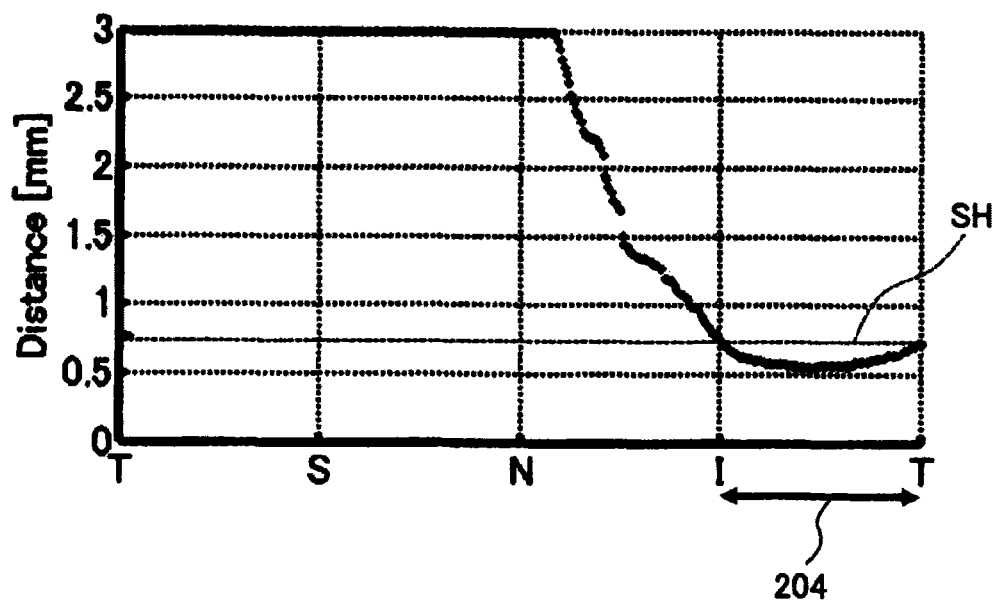
FIG. 10 is a schematic diagram for explaining an operation of a fundus observation apparatus according to an embodiment.

Modes of displaying the ratio information are explained. FIGS. 9 and 10 illustrate examples of displaying the ratio information. In FIG. 9, ratio information 203 consisting of an arrow indicating the range of the specified directions is presented on the abnormal region distribution image illustrated in FIG. 6. Further, in FIG. 10, ratio information 204 consisting of an arrow indicating the range of the specified directions on the horizontal axis of the distribution information illustrated in FIG. 5 is presented. Moreover, in FIG. 10, threshold SH that is applied for obtaining this ratio information 204 is presented. Further, although illustration is omitted, it is possible to display, as ratio information, a numerical value indicating the number of the specified directions, the angles thereof, the above quotient or ratio, or the like.

Figure 11:
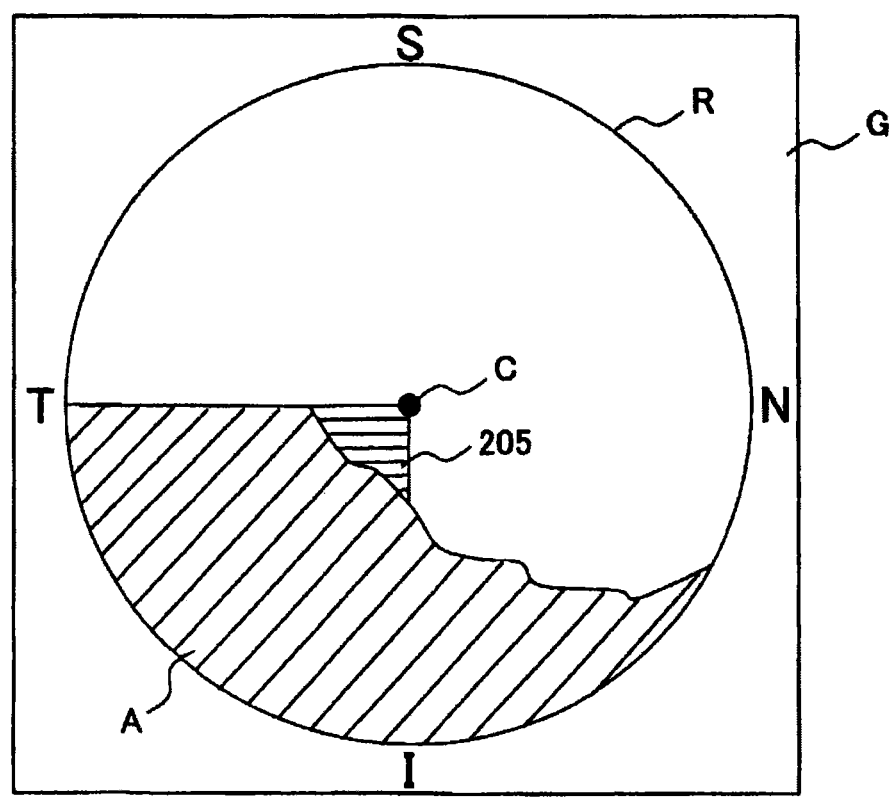
FIG. 11 is a schematic diagram for explaining an operation of a fundus observation apparatus according to an embodiment.

Next, the size information in the example (2) is explained. As described above, the size information expresses the size of normal region located between an abnormal region and central fovea in the direction in which the distance between a central fovea and abnormal region is equal to or less than a threshold. This normal region is a region indicated by symbol 205 in FIG. 11. It should be noted that FIG. 11 is an example of a mode of displaying the size region.

When size information is generated, the evaluation information generating part 235 firstly compares respective distances included in the distribution information with a threshold to specify distances that are equal to or less than this threshold. Next, the evaluation information generating part 235 specifies the direction corresponding to each of the specified directions by referring to the distribution information. Then, the evaluation information generating part 235 identifies the region between the central fovea and abnormal region for each of the specified directions. The identified region corresponds to a normal region. The total sum of the normal regions thus obtained for the respective directions is regarded as the size information.

Size information may be the total sum of the values of areas of such normal regions, may be the ratio between the area of normal regions and the area of abnormal regions in all the specified directions, or may be the ratio between the whole area of all the specified directions and the area of normal regions. Further, since the whole area is the sum of abnormal regions and normal regions, size information may be the ratio between whole area of all the specified directions and the area of abnormal regions. Moreover, volume may be used instead of area. The volume may be a volume of a layer region used for generating layer thickness information, or may be a volume of other layer regions. Modes of displaying size information are not limited to the way illustrated in FIG. 11, and may be presentation of any of the above calculation results by a numerical value.

The statistic in the example (3) is explained. This statistic is a value statistically calculated from the thickness of a layer region in a normal region specified in the same way as the example (2). This layer region is arbitrary as in example (2). Examples of this statistic include a mean value, maximum value, minimum value, variance, standard deviation, median, etc. Further, this statistic is not necessarily a single value, and may include two or more values. For example, two or more or the multiple statistics exemplified above may be included, or a certain number of values from the largest one (and/or the smallest one) in order may be included. The main controller 211 displays the statistic(s) calculated by the evaluation information generating part 235 on the display 240A.

(Third Example of Evaluation Information)

In the third example of evaluation information, multiple directions included in distribution information are divided into two or more groups, and evaluation information is generated for each of the groups. Mode of dividing multiple directions is set in advance. The mode of division may be a default setting, or may be arbitrarily set by a user. Further, multiple modes of division selectable by a user may be provided in advance. In the present embodiment, the scanning region R is divided into four areas (quadrants). It should be noted that mode of dividing the scanning region R (that is, mode of dividing the multiple directions) is not limited to this, and the number of partitions and region (directions) to be divided are arbitrary.

Examples of such evaluation information include the following:

(1) a statistic of distance between an abnormal region and central fovea with respect to each of the two or more groups;
(2) size information that expresses the size of a normal region located between an abnormal region and central fovea with respect to each of the two or more groups;
(3) a statistic of thickness of an arbitrary layer region in the normal region with respect to each of the two or more groups;
(4) ratio information that expresses the ratio of abnormal regions to an image region of the concerned group with respect to each of the two or more groups;
(5) size information that expresses the size of an abnormal region with respect to each of the two or more groups; and
(6) a statistic of the thickness of an arbitrary layer region in an abnormal region with respect to each of the two or more groups;

The statistic of distance in the example (1) is explained. The distance between an abnormal region and central fovea in the respective directions is calculated as described above. For each of the groups, the evaluation information generating part 235 calculates the statistic of distance in direction included in the concerned group. Examples of this statistic include a mean value, maximum value, minimum value, variance, standard deviation, median, etc. Further, this statistic is not necessarily a single value, and may include two or more values. The main controller 211 displays the calculated statistic(s) on the display 240A.

Figure 12:
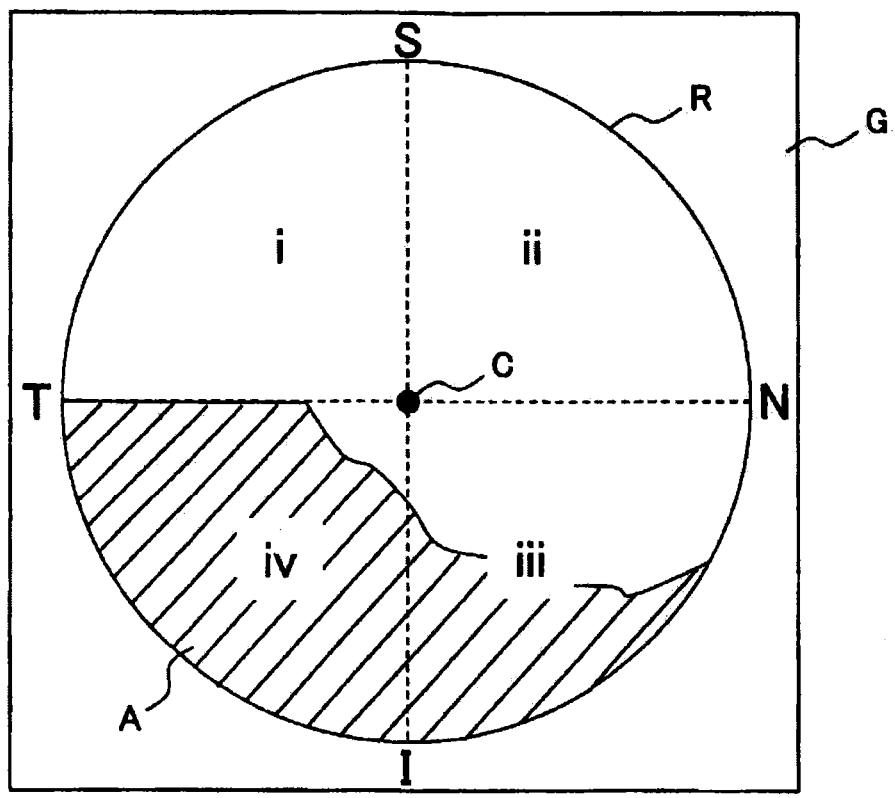
FIG. 12 is a schematic diagram for explaining an operation of a fundus observation apparatus according to an embodiment.

In the example illustrated in FIG. 12, a statistic of distance is obtained for each of four groups i to iv. When the statistic shows a specific direction as in the case of maximum value or minimum value, this direction may be presented. In the example illustrated in FIG. 12, for example, such direction is indicated by a line segment extending from the central fovea in this direction.

Figure 13:
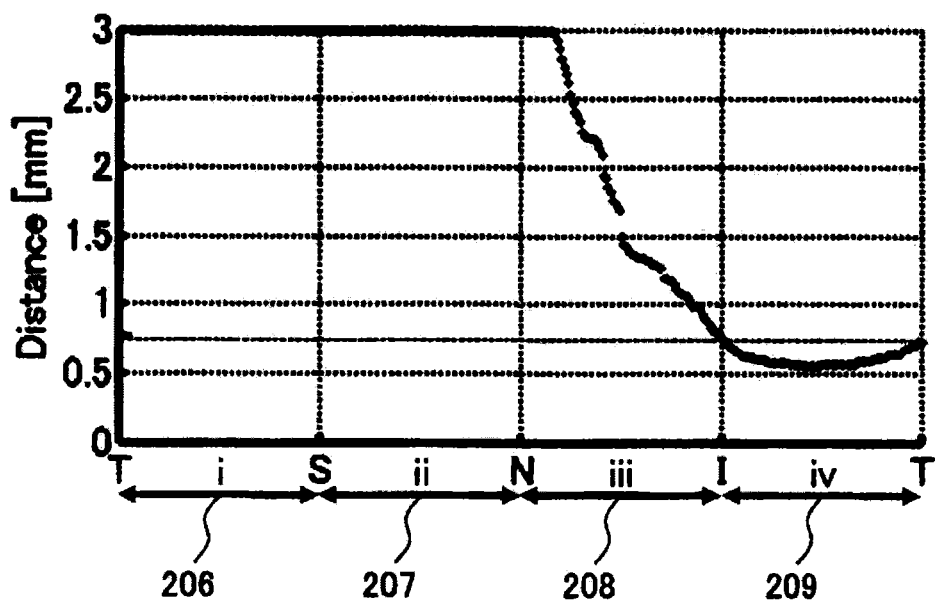
FIG. 13 is a schematic diagram for explaining an operation of a fundus observation apparatus according to an embodiment.

Further, as shown in FIG. 13, it is possible to present multiple groups by dividing the horizontal axis of distribution information into the multiple groups (four groups 206 to 209 in this case). In this example, it is possible to present a maximum value and/or minimum value by a line segment extending, in parallel with the vertical axis, from the position on the horizontal axis corresponding to the concerned direction, for example.

The size information in the example (2) is explained. This size information is calculated as in "second example of evaluation information" for each of the multiple groups. The main controller 211 displays the calculated size information on the display 240A.

The statistic of thickness in the example (3) is explained. This statistic is calculated as in "second example of evaluation information" for each of the multiple groups. The main controller 211 displays the calculated statistic on the display 240A.

The ratio information in the example (4) expresses the ratio of an abnormal region in the image region of each of the groups. For example, this ratio information is calculated by, for each of the groups, dividing the area of the image region that is judged to be an abnormal region by the area of the image region of this group. For example, with respect to the quadrant (group) iii in the example illustrated in FIG. 12, calculation of dividing the area of the shaded region in the quadrant iii by the area of the quadrant iii is carried out.

As another example of the ratio information, it is possible to, for each of the groups, divide the number of directions in which an abnormal region exists by the number of all the directions included in the concerned group. It should be noted that the numerator of this quotient may be limited to directions in which distance between a central fovea and abnormal region is equal to or less than a preset threshold.

The main controller 211 displays any of ratio information calculated as above on the display 240A.

The size information in the example (5) expresses the size of an abnormal region. Processing of calculating this size information may be carried out as in the case of the size information of a normal region in the example (2). The main controller 211 displays the calculated size information of the abnormal region on the display 240A.

The statistic in the example (6) is obtained by statistically processing the thickness of an arbitrary layer region in an abnormal region for each of the groups. Examples of this statistic include a mean value, maximum value, minimum value, variance, standard deviation, median, etc. Further, this statistic is not necessarily a single value, and may include two or more values. The main controller 211 displays the calculated statistic(s) on the display 240A.

The image processor 230 that functions as above comprises, for example, the aforementioned microprocessor, RAM, ROM, hard disk drive, circuit board, and so on. A computer program that causes the microprocessor to perform the above functions is stored in the storage device such as the hard disk drive in advance.

(User Interface)

A user interface 240 comprises the display 240A and the operation part 240B. The display 240A is configured to include a display device of the aforementioned arithmetic and control unit 200 and/or the display device 3. The operation part 240B is configured to include an operation device of the aforementioned arithmetic and control unit 200. The operation part 240B may also comprise various kinds of buttons, keys, etc. that are provided with the case of the fundus observation apparatus 1 or outside thereof. For example, when the retinal camera unit 2 has a case that is similar to conventional retinal cameras, a joy stick, operation panel, etc. provided with the case may also be included in the operation part 240B. Furthermore, the display 240A may also include various display devices such as a touch panel monitor etc. provided with the case of the retinal camera unit 2.

The display 240A and the operation part 240B do not need to be configured as separate components. For example, like a touch panel monitor, it is possible to apply a device in which the display function and the operation function are integrated. In this case, the operation part 240B is configured to include a touch panel monitor and a computer program. A content of operation to the operation part 240B is input into the controller 210 as an electrical signal. Further, operations and/or information input may be carried out by using a graphical user interface (GUI) displayed on the display 240A and the operation part 240B.

[Scanning with Signal Light and OCT Images]

Here, scanning with the signal light LS and OCT image are explained.

The scanning modes of the signal light LS by the fundus observation apparatus 1 may include, for example, horizontal scan, vertical scan, cruciform scan, radial scan, circular scan, concentric scan, helical scan, etc. These scanning modes are selectively used as necessary taking into account an observation site of a fundus, an analysis target (retinal thickness etc.), time required for scanning, the density of scanning, and so on.

The horizontal scan is one for scanning the signal light LS in the horizontal direction (x-direction). The horizontal scan includes a mode of scanning the signal light LS along multiple scanning lines extending in the horizontal direction arranged in the vertical direction (y-direction). In this mode, the interval of scanning lines may be arbitrarily set. Further, by setting the interval between adjacent scanning lines to be sufficiently narrow, it is possible to form the aforementioned three-dimensional image (three-dimensional scan). The vertical scan is performed in a similar manner.

The cruciform scan is one for scanning the signal light LS along a cross-shape trajectory consisting of two linear trajectories (line trajectories) orthogonal to each other. The radial scan is one for scanning the signal light LS along a radial trajectory consisting of multiple line trajectories arranged at predetermined angles. It should be noted that the cruciform scan is an example of the radial scan.

The circular scan is one for scanning the signal light LS along a circular trajectory. The concentric scan is one for scanning the signal light LS along multiple circular trajectories arranged concentrically around a predetermined center position. The circular scan is an example of the concentric scan. The helical scan is one for scanning the signal light LS along a helical trajectory while making the turning radius gradually smaller (or greater).

Since the galvano scanner 42 is configured to scan the signal light LS in the directions orthogonal to each other, the galvano scanner 42 is capable of scanning the signal light LS in the x-direction and the y-direction independently. Moreover, it is possible to scan the signal light LS along an arbitrary trajectory on the xy-plane by simultaneously controlling the directions of two galvano mirrors included in the galvano mirror 42. Thus, various kinds of scanning modes as described above may be realized.

By scanning the signal light LS in the modes described above, it is possible to obtain a cross sectional image in the plane spanned by the direction along the scanning line and the depth direction (z-direction) of the fundus. Moreover, in a case in which the interval between scanning lines is narrow, it is possible to obtain the aforementioned three-dimensional image.

A region on the fundus Ef subjected to scanning by the signal light LS as above, that is, a region on the fundus Ef subjected to OCT measurement, is referred to as a scanning region. A scanning region for the three-dimensional scan is a rectangular-shaped region in which multiple horizontal scans are arranged. Furthermore, a scanning region for the concentric circular scan is a disc-shaped region surrounded by the trajectories of a circular scan of a maximum diameter. Moreover, the scanning region for the radial scan is a disc-shaped (or polygonal-shaped) region linking end positions of the scanning lines.

[Operation]

Figure 14:
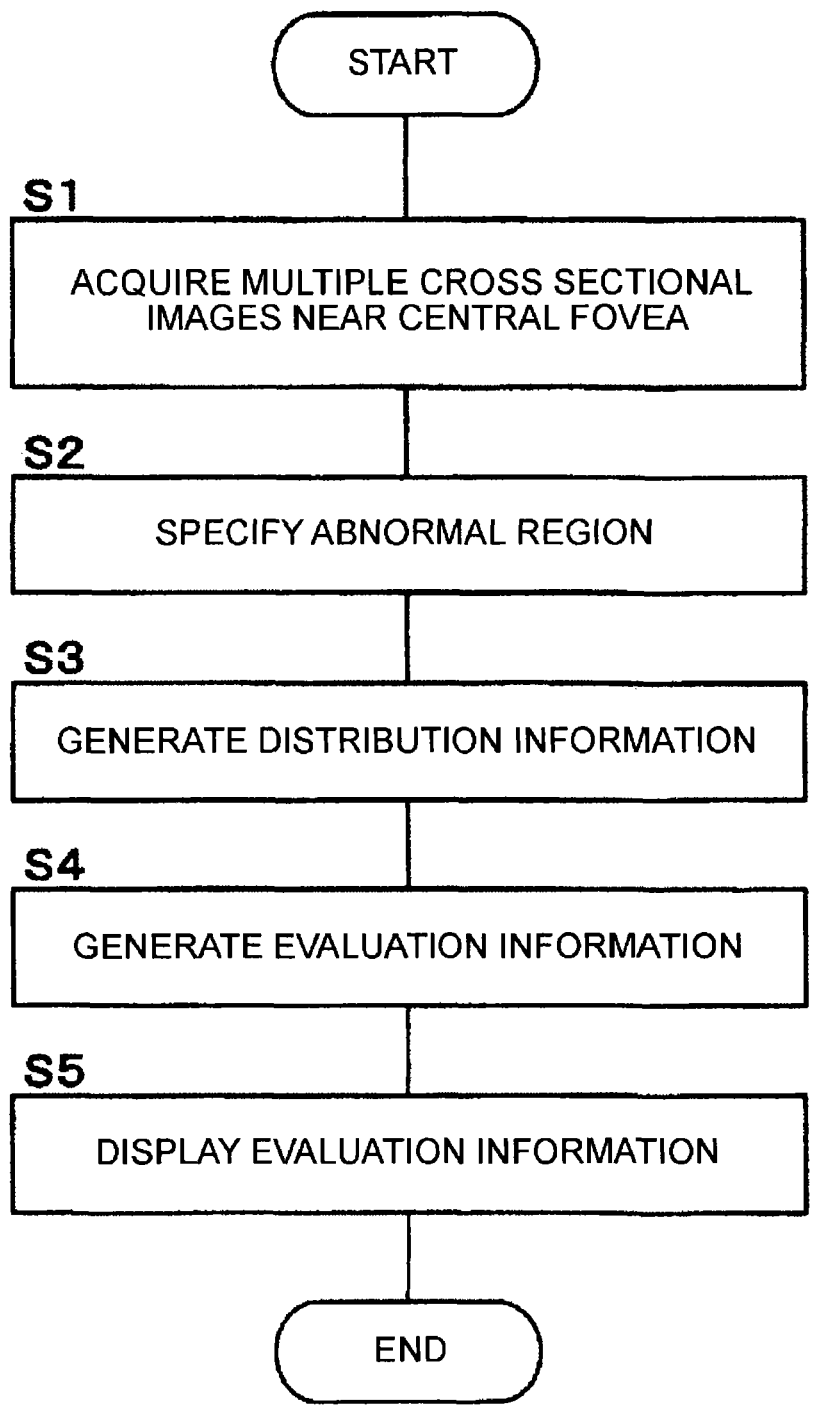
FIG. 14 is a flowchart showing an example of an operation of a fundus observation apparatus according to an embodiment.

An operation of the fundus observation apparatus 1 is described. FIG. 14 illustrates an example of the operation of the fundus observation apparatus 1. It is assumed that alignment and focusing have already done and a fixation target for macula is being presented to the eye. It should be noted that the flow of processes is simply described below since each process has been described in detail.

(S1: Acquire Multiple Cross Sectional Images Near Central Fovea)

First, the main controller 211 controls the galvano scanner 42 etc. to scan the vicinity of the central fovea of the fundus Ef with the signal light LS. This scanning is radial scan centered at the central fovea, for example. The image forming part 220 forms multiple cross sectional images corresponding to this scanning mode.

(S2: Specify Abnormal Region)

Next, the image processor 230 specifies an abnormal region based on the multiple cross sectional images acquired in the step 1. This processing includes processing of specifying a layer region by the layer region specifying part 231, processing of generating layer thickness information by the layer thickness information generating part 232, and processing of specifying an abnormal region by the abnormal region specifying part 233.

(S3: Generate Distribution Information)

Subsequently, the distribution information generating part 234 generates distribution information based on the abnormal region specified in the step 2. This processing includes processing of calculating the distance between the central fovea and the abnormal region for each of the cross sectional images, and processing of associating the direction of the respective cross section with the distance. Thereby, distribution information as shown in FIG. 5 is obtained.

(S4: Generate Evaluation Information)

Next, the evaluation information generating part 235 generates evaluation information based on the distribution information generated in the step 3. The evaluation information generated here is at least one of the aforementioned examples. It may be configured that a kind(s) of evaluation information to be generated is designated in advance.

(S5: Display Evaluation Information)

The main controller 211 displays the evaluation information generated in the step 4 on the display 240A. Display modes thereof are described above. It may be configured to generate multiple kinds of evaluation information in the step 4 and selectively display evaluation information of a kind(s) designated by using the operation part 240B.

[Effects]

Effects of the fundus observation apparatus 1 are explained.

The fundus observation apparatus 1 comprises the optical system, image forming part 220, layer region specifying part 231, layer thickness information generating part 232, abnormal region specifying part 233, distribution information generating part 234 and evaluation information generating part 235. The optical system divides light from the light source unit 101 into the signal light LS and reference light LR, generates the interference light LC by superposing the signal light LS having traveled by way of the fundus Ef and the reference light LR having traveled by way of the reference optical path, and detects the interference light LC. The image forming part forms a cross sectional image of the fundus Ef based on detection results of the interference light LC. The layer region specifying part 231, layer thickness information generating part 232 and abnormal region specifying part 233 analyze the cross sectional image to specify an abnormal region located in the vicinity of central fovea of the fundus Ef. The distribution information generating part 234 calculates the distance between the central fovea and the abnormal region, and generates association information in which the direction of the abnormal region relative to the central fovea and the distance are associated with each other. The evaluation information generating part 235 generates evaluation information for evaluating the state of the fundus Ef based on the association information.

Here, the image forming part 220, for example, forms multiple cross sectional images of multiple cross sections located in the vicinity of the central fovea of the fundus Ef based on detection results of the interference light LC. Further, the distribution information generating part 234 calculates, for each of the multiple cross sectional images, the distance between the central fovea and the abnormal region in the concerned cross section, and generates, as the association information, distribution information that represents distribution of distances in multiple directions corresponding to the multiple cross sections, for example. The evaluation information generating part 235 generates the evaluation information based on the distribution information.

According to the fundus observation apparatus 1 thus configured, it is possible to obtain evaluation information based on distribution state of abnormal regions in the vicinity of the central fovea. By carrying out such examination instead of visual field test, objective data for center management may be provided while considering reduction of examination time.

Second Embodiment

A fundus observation apparatus of the present embodiment provides evaluation information different from those in the first embodiment. Evaluation is performed based on distribution of abnormal regions in sites that are a preset distance away from a central fovea in the present embodiment while evaluation is performed based on the distance between a central fovea and abnormal region in the first embodiment.

Figure 15:
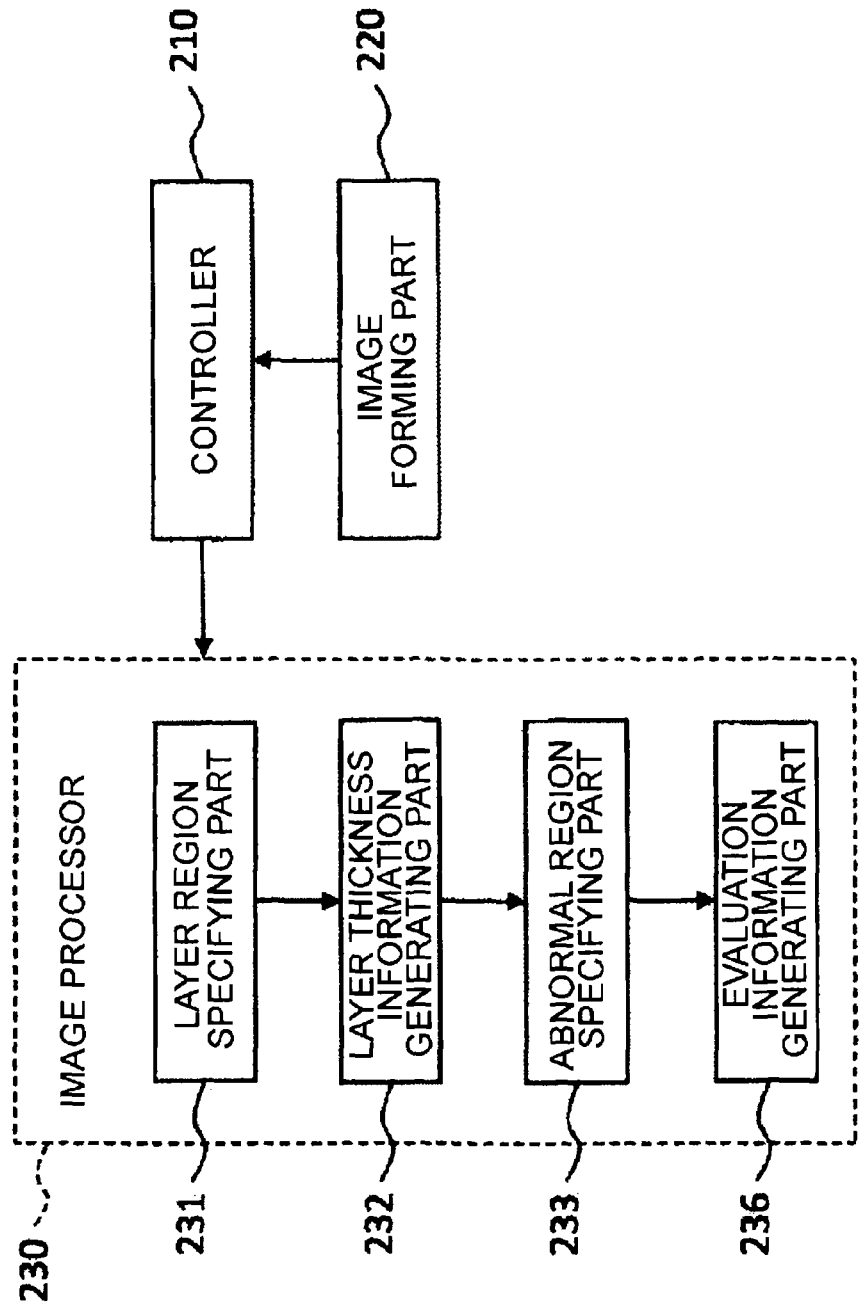
FIG. 15 is a schematic block diagram showing an example of a configuration of a fundus observation apparatus according to an embodiment.

The fundus observation apparatus of the present embodiment comprises an optical system similar to that in the first embodiment (see FIGS. 1 and 2). On the other hand, the fundus observation apparatus of the present embodiment comprises image processor different from that in the first embodiment. FIG. 15 illustrates an example of configuration of the present embodiment. Same symbols are assigned to components which carry out same processing as the first embodiment. Components of control system omitted in FIG. 15 are same as those in the first embodiment (see FIG. 3). The arithmetic and control unit 200 comprising such configuration (image processor 230) corresponds to an example of "fundus image analyzing apparatus".

The image processor 230 is provided with a layer region specifying part 231, layer thickness information generating part 232, abnormal region specifying part 233 and evaluation information generating part 236. Each of the layer region specifying part 231, layer thickness information generating part 232 and abnormal region specifying part 233 carries out same processing as in the first embodiment. On the other hand, although details are described later, the evaluation information generating part 236 carries out different processing from the evaluation information generating part 235. It should be noted that configuration in which both evaluation information generating part 235 and 236 are installed may be applied.

Operations of the fundus observation apparatus of the present embodiment are described. In the present embodiment, a cross section(s) located in the vicinity of the central fovea of the fundus Ef is scanned with the signal light LS. This cross section may be a cross section along a preset circle substantially centered at the central fovea (object circle), or may be a cross section intersecting with the object circle at multiple points. When scanning a cross section along the object circle, circle scan is applied, for example. Further, when scanning a cross section intersecting with the object circle at multiple points, radial scan or three-dimensional scan is applied, for example.

Figure 16:
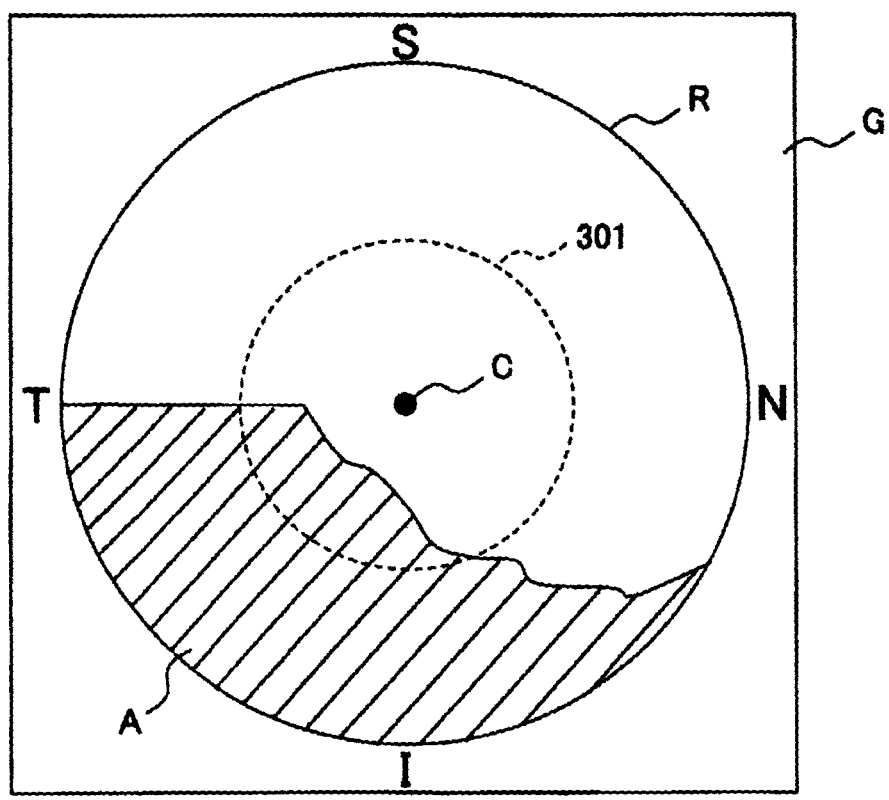
FIG. 16 is a schematic diagram for explaining an operation of a fundus observation apparatus according to an embodiment.

A circle 301 illustrated in FIG. 16 is an example of the object circle. The object circle has preset diameter (such as diameter of 3 mm). Position matching between the center of the object circle and the central fovea may be carried out by using a fixation target for macula or by using registration between a fundus image and an OCT image in the same manner as the first embodiment. Further, the position of the central fovea may be identified from an OCT image itself by considering the fact that central fovea is the center position of macula, that is, the fact that central fovea is the deepest location of the hollow corresponding to macula.

Based on detection results of the interference light LC acquired by the above scanning, the image forming part 220 forms a cross sectional image that depicts a cross section to which the scanning has been applied. At this time, it may be configured to image only common portions between the cross section and the object circle (that is, the multiple points of intersection described above).

The layer region specifying part 231 analyzes a cross sectional image generated by the image forming part 220 to specify a layer region in the cross section along the object circle. The layer thickness information generating part 232 analyzes the specified layer region to generate layer thickness information related to the thickness of the layer region. The abnormal region specifying part 233 specifies an abnormal region based on the layer thickness information. The layer region specifying part 231, layer thickness information generating part 232 and abnormal region specifying part 233 function as an example of "specifying part". It should be noted that the specifying part may be configured to specify a normal region in addition to or instead of specification of abnormal region.

It should be noted that, in the above, it may be configured to process only data on the object circle or to process other data in addition to it. Configuration is sufficient for the present embodiment in which the result of judgment of abnormal/normal at the multiple on the object circle may be provided to the evaluation information generating part 236.

The evaluation information generating part 236 is explained. The evaluation information generating part 236 generates evaluation information that includes at least one of the following information:

(1) length of an abnormal region
(2) length of a normal region
(3) ratio of the length of an abnormal region to the length of the object circle
(4) ratio of the length of a normal region to the length of the object circle
(5) difference between the length of an abnormal region and the length of a normal region
(6) ratio between the length of an abnormal region and the length of a normal region The information (1) is explained. The length of an abnormal region may be calculated based on distribution of points that are determined to be an abnormal region from among the above multiple points on the object circle. That is, since the length of the circumference of the object circle is preset, the length of an abnormal region may be calculated based on the length of the object circle or based on unit length obtained from the length of the object circle. When there are multiple abnormal regions, the sum of the lengths of these abnormal regions may be regarded as the calculation result.

The information (2) is explained. The length of a normal region may be calculated in the same manner as that of an abnormal region. It should be noted that since abnormal regions are specified in the present embodiment, other portions than portions that are judged as abnormal regions on the object circle correspond to normal regions. In contrast, in the case in which it is configured to specify normal regions, other portions than portions that are judged as normal regions on the object circle correspond to abnormal regions.

The information (3) is explained. The ratio of the length of the abnormal region to the length of the object circle may be obtained by dividing the length of the abnormal region calculated in the same manner as the above information (1) by the preset length of the object circle.

The information (4) is explained. The ratio of the length of the normal region to the length of the object circle may be obtained by dividing the length of the normal region calculated in the same manner as the above information (2) by the preset length of the object circle.

The information (5) is explained. The difference between the length of the abnormal region and the length of the normal region is obtained by calculating the difference between the length of the abnormal region calculated in the same manner as the above information (1) and the length of the normal region calculated in the same manner as the above information (2). Here, the calculation may be subtraction of the length of preset one of the abnormal region and the normal region from the length of the other, or may be calculation of the absolute value of a difference between the abnormal region and the normal region in any order. In the former case, the difference of the length of one image region from the length of the other image region is obtained, and the difference value may become a negative value. On the other hand, in the latter case, the difference value calculated does not become a negative value.

The information (6) is explained. The ratio between the length of the abnormal region and the length of the normal region is obtained by calculating the ratio between the length of the abnormal region calculated in the same manner as the above information (1) and the length of the normal region calculated in the same manner as the above information (2). Here, the ratio of the length of preset one of the abnormal region and the normal region to the length of the other is calculated. Namely, the ratio of the length of the normal region to the length of the abnormal region is calculated, or the ratio of the length of the abnormal region to the length of the normal region is calculated.

Figure 17:
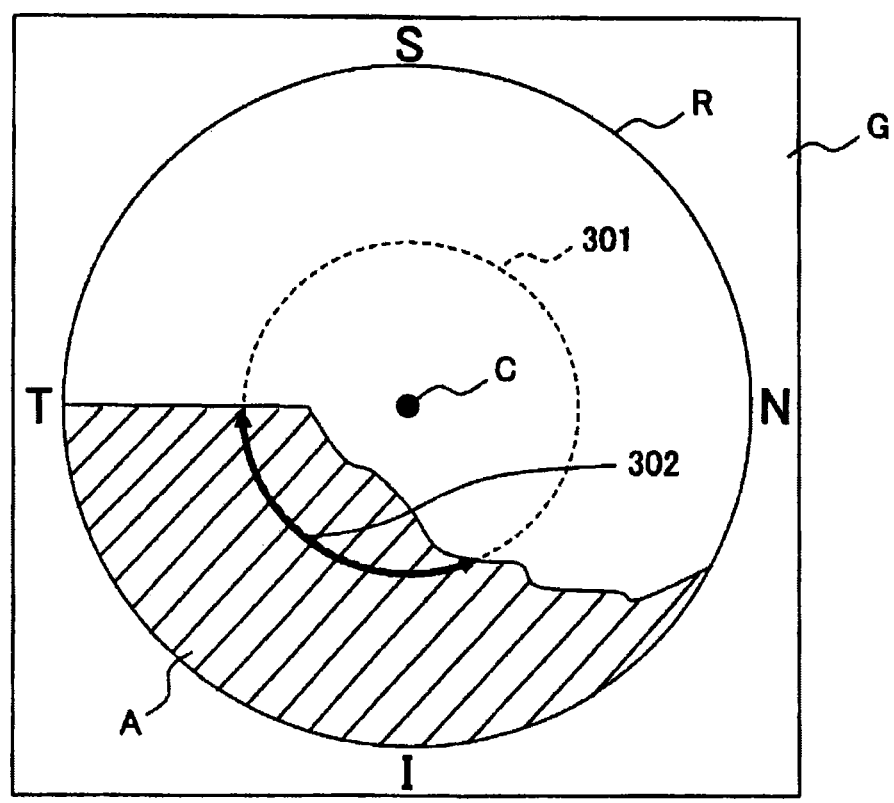
FIG. 17 is a schematic diagram for explaining an operation of a fundus observation apparatus according to an embodiment.

The main controller 211 displays the evaluation information calculated as above on the display 240A. Further, as illustrated in FIG. 17, information that expresses the common region between an object circle 301 and an abnormal region A, more specifically, information 302 that expresses distribution of abnormal region on the object circle 301 may be displayed on the display 240A.

Effects of the fundus observation apparatus of the present embodiment are explained. The fundus observation apparatus comprises the optical system, image forming part 220, specifying part and evaluation information generating part 236. The optical system divides light from the light source unit 101 into the signal light LS and reference light LR, generates the interference light LC by superposing the signal light LS having traveled by way of the fundus Ef and the reference light LR having traveled by way of the reference optical path, and detects the interference light LC. The image forming part forms a cross sectional image of a cross section along a circle (object circle 301) centered at central fovea C of the fundus Ef based on detection results of the interference light LC. The specifying part analyzes the cross sectional image to specify an abnormal region and/or normal region in the cross section along the circle. The evaluation information generating part 236 generates evaluation information for evaluating the state of the fundus Ef including at least one of: the length of the abnormal region and/or normal region; ratio of the length of the abnormal region and/or normal region to the length of the circle; and the difference or ratio between the length of the abnormal region and the length of the normal region.

Moreover, the specifying part may comprise the layer region specifying part 231 configured to analyze the cross sectional image to specify a layer region in the cross section along the circle and the layer thickness information generating part 232 configured to analyze the layer region to generate layer thickness information related to thickness thereof, and further the specifying part specifies the abnormal region and/or normal region based on the layer thickness information.

According to the fundus observation apparatus thus configured, it is possible to obtain evaluation information based on distribution state of abnormal regions in the vicinity of the central fovea. By carrying out such examination instead of visual field test, objective data for center management may be provided while considering reduction of examination time.

<Fundus Image Analyzing Apparatus>

An embodiment of a fundus image analyzing apparatus is explained. The fundus image analyzing apparatus may be realized as part of a fundus observation apparatus such as the arithmetic and control unit 200 in the above embodiments. Alternatively, it is possible to apply a fundus image analyzing apparatus that does not comprise a function for OCT measurement and/or fundus photography.

The first example of fundus image analyzing apparatus comprises a receiving part, specifying part, association information generating part and evaluation information generating part. The receiving part is configured to receive a cross sectional image of an eye fundus. Examples of the receiving part include a communication interface and a drive apparatus. The specifying part is configured to analyze the cross sectional image to specify an abnormal region located in the vicinity of central fovea of the eye fundus. The association information generating part has the same function as that in the first embodiment, for example, and is configured to calculate the distance between the central fovea and the abnormal region and generate association information in which the direction of the abnormal region relative to the central fovea and the distance are associated with each other. The evaluation information generating part has the same function as that in the first embodiment, for example, and is configured to generate evaluation information for evaluating the state of the eye fundus based on the association information.

The second example of fundus image analyzing apparatus comprises a receiving part, specifying part, and evaluation information generating part. The receiving part is configured to receive a cross sectional image of a cross section along a circle around central fovea of an eye fundus. The receiving part may be the same device as the first example. The specifying part is configured to analyze the cross sectional image to specify an abnormal region and/or normal region in the cross section along the circle as in the second embodiment. The evaluation information generating part is configured to generate evaluation information for evaluating the state of the eye fundus including at least one of: the length of the abnormal region and/or normal region; ratio of the length of the abnormal region and/or normal region to the length of the circle; and the difference or ratio between the length of the abnormal region and the length of the normal region as in the second embodiment.

According to the fundus image analyzing apparatus thus configured, it is possible to obtain evaluation information based on distribution state of abnormal regions in the vicinity of the central fovea. By carrying out such examination instead of visual field test, objective data for center management may be provided while considering reduction of examination time.

Modification Examples

The configuration described above is merely illustrations for favorably implementing the present invention. Therefore, it is possible to make arbitrary modification (omission, replacement, addition, etc.) within the scope of the present invention.

In the above embodiment, the optical path length difference between the optical path of the signal light LS and the optical path of the reference light LR is changed by varying the position of the optical path length changing part 41; however, a method for changing the optical path length difference is not limited to this. For example, it is possible to change the optical path length difference by providing a reference mirror (reference mirror) in the optical path of the reference light and moving the reference mirror in the advancing direction of the reference light to change the optical path length of the reference light. Further, the optical path length difference may be changed by moving the retinal camera unit 2 and/or the OCT unit 100 with respect to the eye E to change the optical path length of the signal light LS. Moreover, in a case that an object is not a living site or the like, it is also effective to change the optical path length difference by moving the object in the depth direction (z-direction).

Computer programs for implementing the above embodiments can be stored in any kind of recording medium that can be read by a computer. As such recording media, for example, an optical disk, a semiconductor memory, a magneto-optic disk (CD-ROM, DVD-RAM, DVD-ROM, MO, and so on), and a magnetic storage (a hard disk, a Floppy Disk™, ZIP, and so on) can be used.

In addition, it is possible to transmit/receive this program through a network such as internet or LAN etc.

EXPLANATION OF SYMBOLS

1 fundus observation apparatus
2 retinal camera unit
10 illumination optical system
30 imaging optical system
42 galvano scanner
100 OCT unit
101 light source unit
115 CCD image sensor
200 arithmetic and control unit
210 controller
211 main controller
212 storage
220 image forming part
230 image processor
231 layer region specifying part
232 layer thickness information generating part
233 abnormal region specifying part
234 distribution information generating part
235 evaluation information generating part
236 evaluation information generating part
240A display
240B operation part
E eye
Ef (eye) fundus
LS signal light
LR reference light
LC interference light

What is claimed is:

1. A fundus observation apparatus, comprising:
   an optical system configured to divide light from a light source into signal light and reference light, generate interference light by superposing the signal light having traveled by way of an eye fundus and the reference light having traveled by way of a reference optical path, and detect the interference light;
   an image forming part configured to form a cross sectional image of the eye fundus based on detection results of the interference light;
   a specifying part configured to analyze the cross sectional image to specify an abnormal region located in the vicinity of central fovea of the eye fundus;
   an association information generating part configured to calculate the distance between the central fovea and the abnormal region and generate association information in which the direction of the abnormal region relative to the central fovea and the distance are associated with each other; and
   an evaluation information generating part configured to generate evaluation information for evaluating the state of the eye fundus based on the association information.

2. The fundus observation apparatus of claim 1, wherein
   the image forming part forms multiple cross sectional images of multiple cross sections located in the vicinity of the central fovea of the eye fundus based on detection results of the interference light,
   the association information generating part comprises a distribution information generating part configured to calculate, for each of the multiple cross sectional images, the distance between the central fovea and the abnormal region in the concerned cross section, and generate, as the association information, distribution information that represents distribution of distances in multiple directions corresponding to the multiple cross sections, and
   the evaluation information generating part generates the evaluation information based on the distribution information.

3. The fundus observation apparatus of claim 2, wherein
   the evaluation information generating part generates, as the evaluation information, graph information that represents the distribution information by coordinate system spanned by a first coordinate axis representing the multiple directions and a second coordinate axis representing the distances, and further comprising:

a display; and a display controller configured to display the graph information on the display.

4. The fundus observation apparatus of claim 2, wherein the evaluation information generating part specifies the minimum value from among the distances included in the distribution information, specifies the direction corresponding to the minimum value from among the multiple directions, and generates the evaluation information based on the direction specified.

5. The fundus observation apparatus of claim 2, wherein the evaluation information generating part specifies the distance that is equal to or less than a preset threshold from among the distances included in the distribution information, specifies the direction corresponding to the distance specified from among the multiple directions, and generates the evaluation information based on the direction specified.

6. The fundus observation apparatus of claim 5, wherein the evaluation information generating part calculates, as the evaluation information, ratio of the directions specified to the multiple directions.

7. The fundus observation apparatus of claim 5, wherein the evaluation information generating part calculates, as the evaluation information, size information that represents the size of a normal region located between the abnormal region and the central fovea in the direction specified.

8. The fundus observation apparatus of claim 7, further comprising:

an imaging part configured to image the surface of the eye fundus;

a display; and a display controller configured to display a surface image of the eye fundus obtained by the imaging part on the display, and display a partial region in the surface image corresponding to the normal region in a different aspect from other regions.

9. The fundus observation apparatus of claim 5, wherein the evaluation information generating part calculates, as the evaluation information, a statistic of the thickness of a layer region in a normal region located between the abnormal region and the central fovea in the direction specified.

10. The fundus observation apparatus of claim 2, wherein the evaluation information generating part divides the multiple directions into two or more groups, and generates the evaluation information for each of the two or more groups.

11. The fundus observation apparatus of claim 10, wherein the evaluation information generating part calculates, as the evaluation information, a statistic of distance between the abnormal region and the central fovea for each of the two or more groups.

12. The fundus observation apparatus of claim 10, wherein the evaluation information generating part calculates, as the evaluation information, size information that represents the size of a normal region located between the abnormal region and the central fovea for each of the two or more groups.

13. The fundus observation apparatus of claim 12, further comprising:

an imaging part configured to image the surface of the eye fundus;

a display; and a display controller configured to display a surface image of the eye fundus obtained by the imaging part on the display, and display a partial region in the surface image corresponding to the normal region in a different aspect from other regions.

14. The fundus observation apparatus of claim 10, wherein the evaluation information generating part calculates, as the evaluation information, a statistic of the thickness of a layer region in a normal region located between the abnormal region and the central fovea for each of the two or more groups.

15. The fundus observation apparatus of claim 10, for each of the two or more groups, the evaluation information generating part calculates, as the evaluation information, ratio of the abnormal region to the image region corresponding to the concerned group.

16. The fundus observation apparatus of claim 10, wherein the evaluation information generating part calculates, as the evaluation information, size information that represents the size of the abnormal region for each of the two or more groups.

17. The fundus observation apparatus of claim 10, wherein the evaluation information generating part calculates, as the evaluation information, a statistic of the thickness of a layer region in the abnormal region for each of the two or more groups.

18. The fundus observation apparatus of claim 1, further comprising:

an imaging part configured to image the surface of the eye fundus;

a display; and a display controller configured to display a surface image of the eye fundus obtained by the imaging part on the display, and display a partial region in the surface image corresponding to the abnormal region in a different aspect from other regions.

19. The fundus observation apparatus of claim 1, wherein the specifying part comprises:

a layer region specifying part configured to analyze the cross sectional image to specify a layer region;

a layer thickness information generating part configured to analyze the layer region to generate layer thickness information related to thickness thereof; and an abnormal region specifying part configured to specify the abnormal region based on the layer thickness information.

20. The fundus observation apparatus of claim 19, wherein the layer thickness information generating part generates, as the layer thickness information, thickness distribution information that represents distribution of thickness of the layer region in the cross section of the eye fundus represented by the cross sectional image.

21. The fundus observation apparatus of claim 19, wherein the layer thickness information generating part generates, as the layer thickness information, symmetric position information that represents difference or ratio of the thicknesses of the layer region at symmetric positions with respect to the central fovea.

22. The fundus observation apparatus of claim 19, wherein when the cross sectional image has been formed for each of the right and left eyes of one patient, the layer thickness information generating part generates, as the layer thickness information, both-eye information that represents difference or ratio of the thicknesses of the layer regions at symmetric positions between the eye fundus of the right eye and the eye fundus of the left eye.

23. The fundus observation apparatus of claim 19, wherein the abnormal region specifying part calculates the size of the abnormal region specified, and determines the abnormal region as a normal region when the size is equal to or less than a preset threshold.

24. A fundus observation apparatus, comprising:
- an optical system configured to divide light from a light source into signal light and reference light, generate interference light by superposing the signal light having traveled by way of an eye fundus and the reference light having traveled by way of a reference optical path, and detect the interference light;
- an image forming part configured to form a cross sectional image of a cross section along a circle around central fovea of the eye fundus based on detection results of the interference light;
- a specifying part configured to analyze the cross sectional image to specify an abnormal region and/or normal region in the cross section along the circle; and
- an evaluation information generating part configured to generate evaluation information for evaluating the state of the eye fundus including at least one of: the length of the abnormal region and/or normal region; ratio of the length of the abnormal region and/or normal region to the length of the circle; and the difference or ratio between the length of the abnormal region and the length of the normal region.

25. The fundus observation apparatus of claim 24, wherein the specifying part comprises:
- a layer region specifying part configured to analyze the cross sectional image to specify a layer region in the cross section along the circle; and
- a layer thickness information generating part configured to analyze the layer region to generate layer thickness information related to thickness thereof, and
- the specifying part specifies the abnormal region and/or normal region based on the layer thickness information.

26. A fundus image analyzing apparatus, comprising:
- a receiving part configured to receive a cross sectional image of an eye fundus of an eye;
- a specifying part configured to analyze the cross sectional image to specify an abnormal region located in the vicinity of central fovea of the eye fundus;
- an association information generating part configured to calculate the distance between the central fovea and the abnormal region and generate association information in which the direction of the abnormal region relative to the central fovea and the distance are associated with each other; and
- an evaluation information generating part configured to generate evaluation information for evaluating the state of the eye fundus based on the association information.

27. A fundus image analyzing apparatus, comprising:
- a receiving part configured to receive a cross sectional image of a cross section along a circle around central fovea of an eye fundus of an eye;
- a specifying part configured to analyze the cross sectional image to specify an abnormal region and/or normal region in the cross section along the circle; and
- an evaluation information generating part configured to generate evaluation information for evaluating the state of the eye fundus including at least one of: the length of the abnormal region and/or normal region; ratio of the length of the abnormal region and/or normal region to the length of the circle; and the difference or ratio between the length of the abnormal region and the length of the normal region.

* * * * *